(12) United States Patent
Kim et al.

(10) Patent No.: US 12,193,867 B2
(45) Date of Patent: Jan. 14, 2025

(54) ADAPTIVE DATA ACQUISITION FOR COMPUTED TOMOGRAPHY SYSTEMS

(71) Applicant: GE PRECISION HEALTHCARE LLC, Milwaukee, WI (US)

(72) Inventors: Changlyong Kim, Brookfield, WI (US); Jiahua Fan, New Berlin, WI (US); Brian J. Breuer, Allenton, WI (US); Håkan Langemark, Stockholm (SE); Jean-Baptiste Thibault, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 435 days.

(21) Appl. No.: 17/686,016

(22) Filed: Mar. 3, 2022

(65) Prior Publication Data

US 2023/0277152 A1 Sep. 7, 2023

(51) Int. Cl.
*A61B 6/00* (2024.01)
*A61B 6/03* (2006.01)
(Continued)

(52) U.S. Cl.
CPC .......... *A61B 6/56* (2013.01); *A61B 6/032* (2013.01); *A61B 6/4241* (2013.01); *A61B 6/4435* (2013.01); *A61B 6/582* (2013.01); *G06T 1/0007* (2013.01); *G06T 3/40* (2013.01); *G16H 30/40* (2018.01)

(58) Field of Classification Search
CPC ......... A61B 6/56; A61B 6/032; A61B 6/4241; A61B 6/4435; A61B 6/582; A61B 6/482; A61B 6/5205; A61B 6/52; A61B 6/4021; A61B 6/4078; A61B 6/4085; A61B 6/4266; A61B 6/54; A61B 6/545; A61B 6/566;
(Continued)

(56) References Cited

U.S. PATENT DOCUMENTS 7,114,850 B2  10/2006  Dong et al.
8,183,535 B2   5/2012  Danielsson et al.
(Continued)

FOREIGN PATENT DOCUMENTS

JP  2018139760 A  9/2018

OTHER PUBLICATIONS

JP application 2023-022052 filed 16FEB2023—Office Action issued Jan. 31, 2024; Machine Translation; 8 pages.
(Continued)

*Primary Examiner* — Courtney D Thomas

(57) ABSTRACT

There is provided a computed tomography imaging system including a gantry including a rotating member on a rotating side, a stationary member on a stationary side, and a data communication system. The rotating member on the rotating side includes an X-ray source configured to emit X-rays, an X-ray detector configured to generate detector data, a data storage unit configured to store the detector data, and processing circuitry configured to process at least part of the stored detector data to generate a processed data set. The stationary member on the stationary side is communicatively coupled to the rotating member on the rotating side, and the data communication system is configured to transfer the processed data set from the rotating member on the rotating side to the stationary member on the stationary side.

21 Claims, 16 Drawing Sheets

(51) Int. Cl.
   *A61B 6/42*    (2024.01)
   *A61B 6/58*    (2024.01)
   *G06T 1/00*    (2006.01)
   *G06T 3/40*    (2006.01)
   *G16H 30/40*   (2018.01)

(58) Field of Classification Search
   CPC ......... G06T 1/0007; G06T 3/40; G16H 30/40; G01T 1/2985; G01V 5/226
   See application file for complete search history.

(56) References Cited

U.S. PATENT DOCUMENTS

| | | |
|---|---|---|
| 8,406,537 B2 | 3/2013 | Breuer et al. |
| 2002/0172228 A1* | 11/2002 | Popescu ............... A61B 6/56 370/503 |
| 2009/0046913 A1 | 2/2009 | Chandra |
| 2011/0150171 A1 | 6/2011 | Breuer |
| 2012/0213328 A1 | 8/2012 | Dolazza |

OTHER PUBLICATIONS

JP2018139760 English Abstract; Espacenet search Jul. 15, 2024; 1 page.

Tapiovaara and Wagner, "SNR and DQE analysis of broad spectrum X-ray imaging", Phys. Med. Biol., vol. 30, No. 6, 1985, pp. 519-529.

Alvarez and Macovski, "Energy-selective reconstructions in X-ray computerised tomography", Phys. Med. Biol. 21, 733, Oct. 1976, 14 pages.

S. Leng, et al., "Dose-efficient ultrahigh-resolution scan mode using a photon counting detector computed tomography system", Journal of Medical Imaging 3(4), 043504, Oct.-Dec. 2016, 11 pages.

Roessl and Proksa, "K-edge imaging in x-ray computed tomography using multi-bin photon counting detectors", Phys. Med. Biol., vol. 52, 2007, pp. 4679-4696.

Knoll, "Radiation Detection and Measurement", Linear and Logic Pulse Functions, Chapter 17, 2000, pp. 632-642.

EP application 23157982.2 filed Feb. 22, 2023—extended Search Report issued Jul. 20, 2023; 7 pages.

* cited by examiner

ADAPTIVE DATA ACQUISITION FOR COMPUTED TOMOGRAPHY SYSTEMS

TECHNICAL FIELD

The proposed technology relates to X-ray technology and X-ray imaging and corresponding calibration, imaging reconstruction and imaging tasks. In particular, the proposed technology relates to a computed tomography (CT) imaging system and method of operating such a CT imaging system, for improved data handling.

BACKGROUND

Radiographic imaging in combination with computed tomography (CT) imaging systems have been used for years in medical applications, such as for medical diagnostics and treatment.

Normally, a CT X-ray imaging system, or simply a CT imaging system includes an X-ray source and an X-ray detector array consisting of multiple detectors comprising one or many detector elements, for independent measuring of X-ray intensities. The X-ray source emits X-rays, which pass through a subject or object to be imaged and are then received by the detector array. The X-ray source and detector array are typically arranged to rotate on a rotating member of a gantry, around the subject or object. The emitted X-rays are attenuated by the subject or object as they pass through, and the resulting transmitted X-rays are measured by the detector. The measured data may then be used to reconstruct images of the subject or object.

It may be useful with a brief overview of an illustrative general X-ray imaging system according to the prior art with reference to FIG. 1A. In this illustrative example the X-ray imaging system 1 comprises an X-ray source 10, an X-ray detector system 20 and an associated image processing system or device 30. In general, the X-ray detector system 20 is configured to register radiation from the X-ray source 10, which optionally has been focused by optional X-ray optics or collimators and passed through an object, a subject or a part thereof. The X-ray detector system 20 is connectable to the image processing system 30 via suitable analog read-out electronics, which is at least partly integrated in the X-ray detector system 20, to enable image processing and/or image reconstruction by the image processing system 30.

By way of example, a conventional CT X-ray imaging system, or simply CT imaging system, includes an X-ray source and an X-ray detector arranged in such a way that projection images of the subject or object can be acquired in different viewing angles covering at least 180 degrees. This is most commonly achieved by mounting the source and detector on a support. e.g., a rotating member of a gantry, that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

FIG. 1B is a schematic diagram illustrating an example of an X-ray imaging system setup according to the prior art, showing projection lines from an X-ray source through an object to an X-ray detector.

A further development of X-ray imaging is energy-resolved X-ray imaging, also known as spectral X-ray imaging, where the X-ray transmission is measured for several different energy levels. This can be achieved by letting the source switch rapidly between two different emission spectra, by using two or more X-ray sources emitting different X-ray spectra, or by using an energy-discriminating detector which measures the incoming radiation in two or more energy levels. An example of such a detector is a multi-bin photon-counting detector, where each registered photon generates a current pulse which is compared to a set of thresholds, thereby counting the number of photons incident in each of a number of energy bins.

A spectral X-ray projection measurement results in a projection image for each energy level. A weighted sum of these projection images can be made to optimize the contrast-to-noise ratio (CNR) for a specified imaging task as described in Tapiovaara and Wagner, "SNR and DQE analysis of broad spectrum X-ray imaging", Phys. Med. Biol. 30, 519.

Another technique enabled by energy-resolved X-ray imaging is basis material decomposition. This technique utilizes the fact that all substances built up from elements with low atomic number, such as human tissue, have linear attenuation coefficients whose energy dependence can be expressed, to a good approximation, as a linear combination of two (or more) basis functions:

$$\mu(E) = \alpha_1 f_1(E) + \alpha_2 f_2(E)$$

where $f_1$ and $f_2$ are basis functions and $\alpha_1$ and $\alpha_2$ are the corresponding basis coefficients. More, generally. $f_i$ are basis functions and $\alpha_i$ are corresponding basis coefficients, where $i=1, \ldots, N$, and where N is the total number of basis functions. If there is one or more element in the imaged volume with high atomic number, high enough for a k-absorption edge to be present in the energy range used for the imaging, one basis function must be added for each such element. In the field of medical imaging, such k-edge elements can typically be iodine or gadolinium, substances that are used as contrast agents.

Basis material decomposition has been described in Alvarez and Macovski, "Energy-selective reconstructions in X-ray computerised tomography", Phys. Med. Biol. 21, 733. In basis material decomposition, the integral of each of the basis coefficients, $A_i = \int_p \alpha_i dl$ for $i=1, \ldots, N$ where N is the number of basis functions, is inferred from the measured data in each projection ray 1 from the source to a detector element. In one implementation, this is accomplished by first expressing the expected registered number of counts in each energy bin as a function of Ai:

$$\lambda_i = \int_{E=0}^{\infty} S_i(E) \exp\left(-\sum_{j=1}^{N} A_j F_j(E)\right) dE$$

Here, ili is the expected number of counts in energy bin i, Eis the energy, S': is a response function which depends on the spectrum shape incident on the imaged object, the quantum efficiency of the detector and the sensitivity of energy bin i to X-rays with energy ff. Even though the term "energy bin" is most commonly used for photon-counting detectors, this formula can also describe other energy resolving X-ray imaging systems such as multi-layer detectors or kVp switching sources.

Then, the maximum likelihood method may be used to estimate Ar., under the assumption that the number of counts in each bin is a Poisson distributed random variable. This is accomplished by minimizing the negative log-likelihood function, see Roessl and Proksa, K-edge imaging in x-ray computed tomography using multi-bin photon counting detectors, Phys. Med. Biol. 52 (2007), 4679-4696:

$$Av, \ldots, An = \underset{A, \ldots, A\Lambda}{\operatorname{argmin}} \sum_{i=1}^{M1} L_i(A1JA_1, \ldots, An) - m\ln.ilIJA!J \ldots \bullet \ldots \bullet AN$$

where mi is the number of measured counts in energy bin i and M" is the number of energy bins.

When the resulting estimated basis coefficient line integral A for each projection line is arranged into an image matrix, the result is a material specific projection image, also called a basis image, for each basis i. This basis image can either be viewed directly (e.g., in projection X-ray imaging) or taken as input to a reconstruction algorithm to form maps of basis coefficients ai inside the object (e.g., in CT imaging). Anyway, the result of a basis decomposition can be regarded as one or more basis image representations, such as the basis coefficient line integrals or the basis coefficients themselves.

CT imaging systems with a rotating section, such as a rotating member of a gantry, typically send all acquired data through data slip rings from the rotating section to a stationary computer, wherein the data is later processed in the stationary computer in order to reconstruct images of the subject or object.

Development in the CT X-ray imaging field makes increasingly high gantry rotation speeds and higher spatial resolution of the detectors possible; with this, the requirements for sufficiently handling the data increases.

As the amount of generated data is increased, a large burden is placed on the traditional CT imaging systems which are not designed for handling the increased data flows. Hence a limitation of the systems is that the large amount of data cannot be handled and transferred fast enough through the slip rings, resulting in e.g., a bottleneck effect which limits the use of the CT imaging system.

Therefore, there is still a general demand for improvements with regard to the data handling of CT imaging systems.

SUMMARY

It is an object to mitigate, alleviate or eliminate one or more of the above-identified deficiencies in the art and disadvantages singly or in any combination and solve at least the above-mentioned problem.

It is a specific object to provide an improved computed tomography (CT) imaging system.

It is also an object to provide a method of operating a CT imaging system.

These and other objects are met by one or more embodiments of the present invention, as defined by the claims.

According to a first aspect there is provided a computed tomography (CT) imaging system comprising a gantry including a rotating member on a rotating side and a stationary member on a stationary side. The rotating member on the rotating side comprises an X-ray source configured to emit X-rays, an X-ray detector configured to generate detector data, a data storage unit configured to store the detector data, and processing circuitry configured to process at least part of the stored detector data to generate a processed data set. The stationary member on the stationary side is communicatively coupled to the rotating member on the rotating side. The CT imaging system further comprises a data communication system configured to transfer the processed data set from the rotating member on the rotating side to the stationary member on the stationary side.

According to a second aspect there is provided a method of operating a CT imaging system. The CT imaging system comprises a rotating side comprising an X-ray source configured to emit X-rays, an X-ray detector, a data storage unit, processing circuitry and a stationary side communicatively coupled to the rotating side via a data communication system. The method comprises generating detector data via the X-ray detector and storing the detector data in the data storage unit. The method further comprises processing the stored detector data, in the processing circuitry, to generate a processed data set. The method further comprises transferring the processed data set from the rotating side to the stationary side via the data communication system.

Hence, the first and the second aspects of the present invention share a common general inventive concept of providing an improved handling of the data processing and/or data transferring performed by CT imaging systems. Namely, by storing data on a rotating side of a CT imaging system, processing at least a part of the data stored on the rotating side in order to generate a processed data set on the stationary side, and transferring or sending the processed data set to the stationary side, in order to get a result of a scan or at least relevant data in a CT imaging system on the stationary side in a faster, more efficient and more versatile manner.

The present invention provides an adaptive procedure, according to which the amount of data to transfer from the rotating side to the stationary side can be selectively adapted. Furthermore, what data to process on the rotating side and the stationary side respectively may be selectively and/or adaptively chosen.

Other advantages will be appreciated when reading the detailed description.

A further scope of applicability of the present disclosure will become apparent from the detailed description given below. However, it should be understood that the detailed description and specific examples, while indicating preferred embodiments of the disclosure, are given by way of illustration only, since various changes and modifications within the scope of the disclosure will become apparent to those skilled in the art from this detailed description.

Hence, it is to be understood that this disclosure is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

DETAILED DESCRIPTION

For a better understanding, it may be useful to continue with an introductory description of non-limiting examples of an overall x-ray imaging system in which data processing and transferring according to the inventive concept may be implemented.

Figure 2:
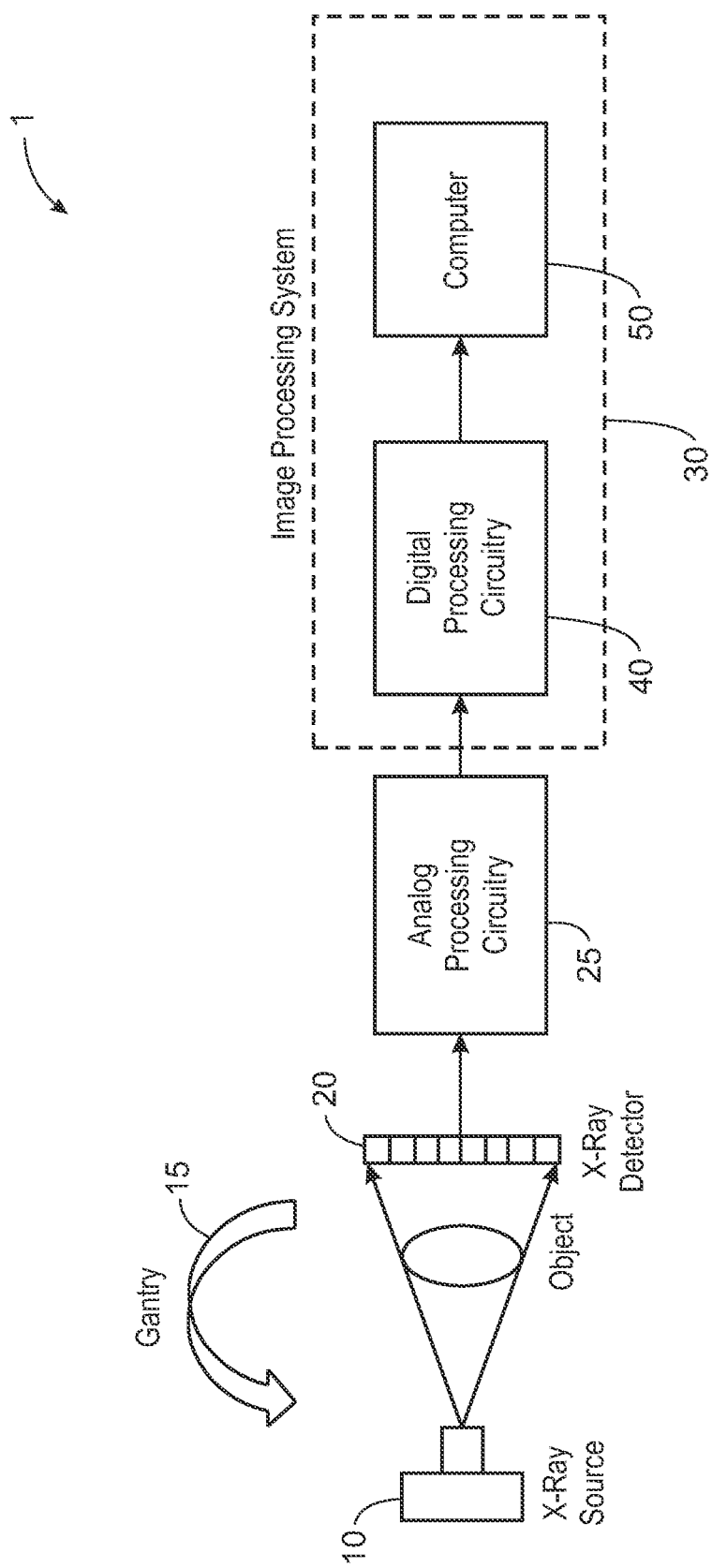
FIG. 2 is a schematic diagram illustrating another example of an x-ray imaging system, such as a CT imaging system.

FIG. 2 is a schematic diagram illustrating an example of a CT imaging system 1 comprising an X-ray source 10, which emits X-rays, an X-ray detector system 20 with an X-ray detector, which detects X-rays after they have passed through the object, analog processing circuitry 25, which processes the raw electrical signals from the X-ray detector and digitizes it, digital processing circuitry 40, which may carry out further processing operations on the measured data, such as applying corrections, storing it temporarily, or filtering, and a computer 50, which stores the processed data and may perform further post-processing and/or image reconstruction. According to an exemplary embodiment, all or part of the analog processing circuitry 25 may be implemented in the X-ray detector system 20. The X-ray source and X-ray detector may be coupled to a rotating member of a gantry 15 of the CT imaging system 1.

The overall X-ray detector may be regarded as the X-ray detector system 20, or the X-ray detector system 20 combined with the associated analog processing circuitry 25.

In communication with and electrically coupled to the analog processing circuitry 25 is an imaging processing system 30, which may include digital processing circuitry 40 and/or a computer 50, which may be configured to perform image reconstruction based on the image data from the X-ray detector. The image processing system 30 may, thus, be seen as the computer 50, or alternatively the combined system of the digital processing circuitry 40 and the computer 50, or possibly the digital processing circuitry 40 by itself if the digital processing circuitry is further specialized also for image processing and/or reconstruction.

An example of a commonly used X-ray imaging system is a CT imaging system, which may include an X-ray source or X-ray tube that produces a fan beam or cone beam of X-rays and an opposing array of X-ray detectors measuring the fraction of X-rays that are transmitted through a patient or object. The X-ray source or X-ray tube and detector array are mounted in a gantry 15 that rotates around the imaged object.

Figure 3:
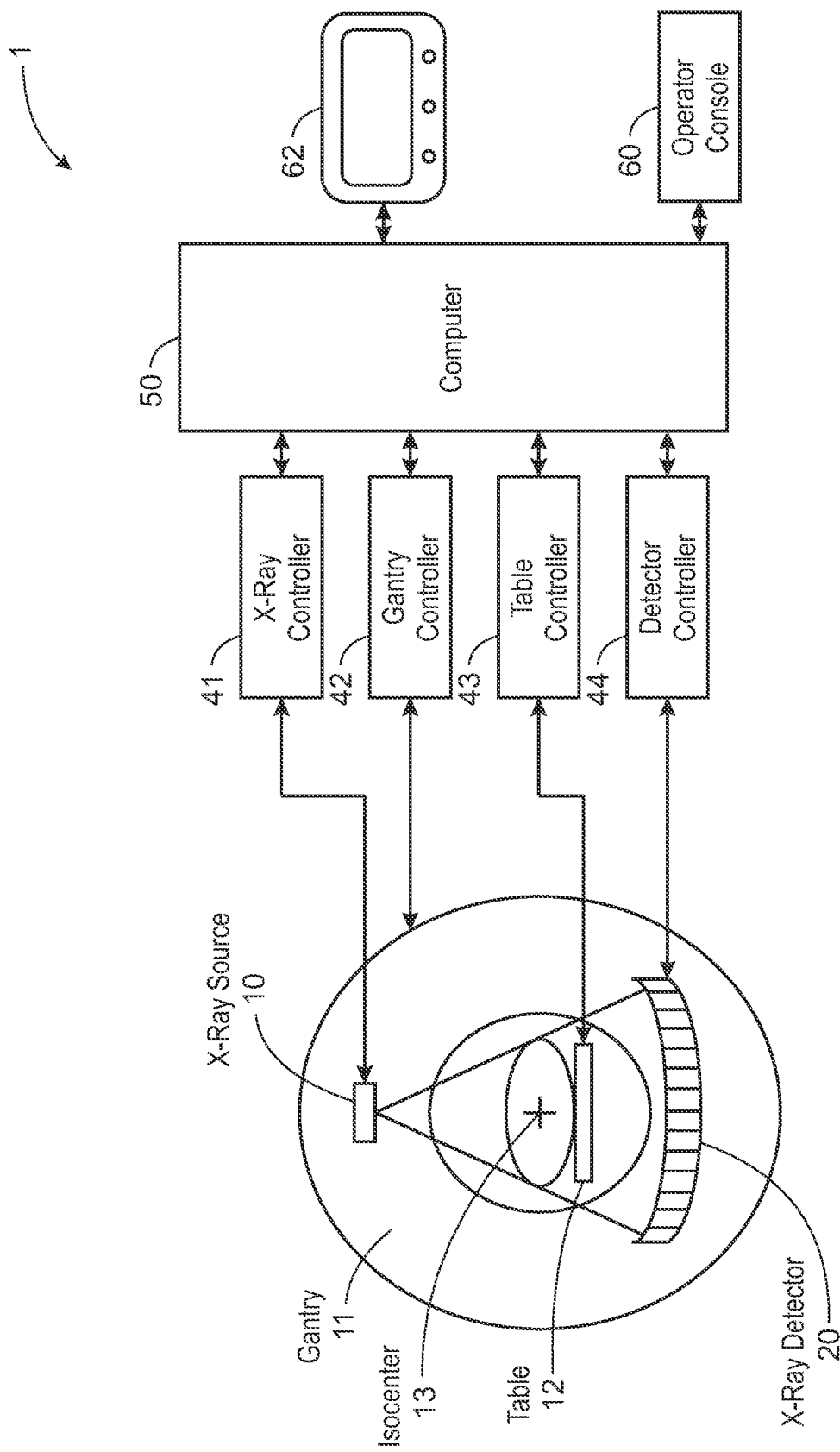
FIG. 3 is a schematic block diagram of a CT imaging system as an illustrative example of an x-ray imaging system.

FIG. 3 schematically shows a CT imaging system 1 as an illustrative example of an X-ray imaging system. The CT imaging system comprises a computer 50 receiving commands and scanning parameters from an operator via an operator console 60 that may have a display 62 and some form of operator interface, e.g., a keyboard, mouse, joystick, touch screen or other input device. The operator supplied commands and parameters are then used by the computer 50 to provide control signals to an X-ray controller 41, a gantry controller 42 and a table controller 43. To be specific, the X-ray controller 41 provides power and timing signals to the x-ray source 10 to control emission of X-rays onto the object or patient lying on the table 12. The gantry controller 42 controls the rotating speed and position of the gantry 11 comprising the X-ray source 10 and the X-ray detector 20. By way of example, the X-ray detector 20 may be a photon-counting X-ray detector. The table controller 43 controls and determines the position of the patient table 12 and the scanning coverage of the patient. There is also a detector controller 44, which is configured for controlling and/or receiving data from the X-ray detector 20.

Figure 1A:
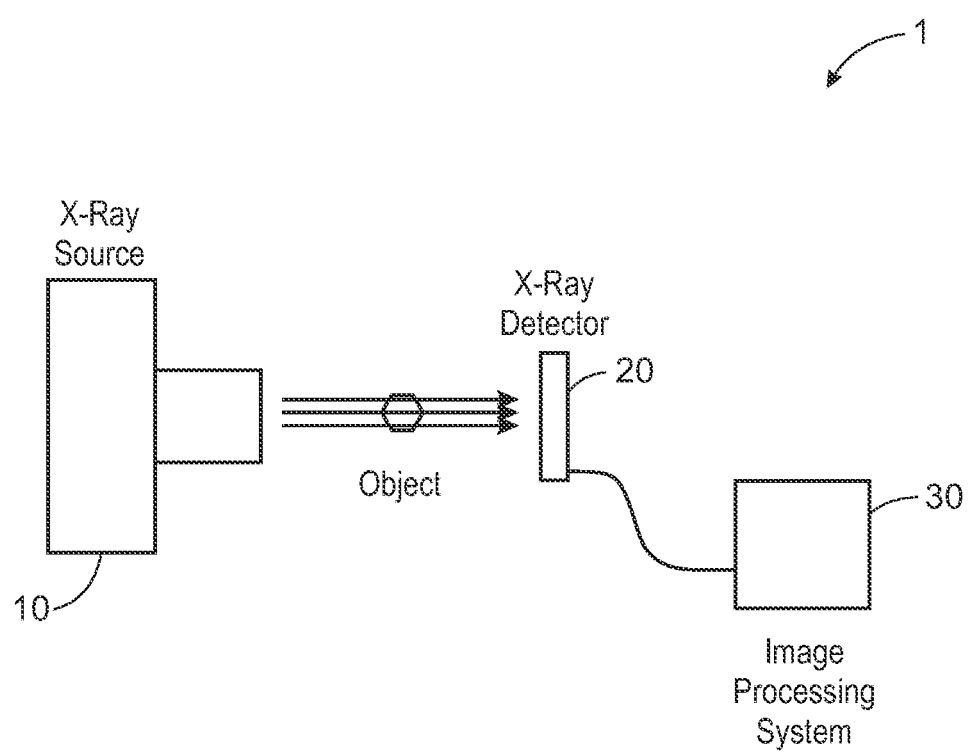
FIGS. 1A and B are schematic diagrams illustrating an example of an overall x-ray imaging system.
Figure 1B:
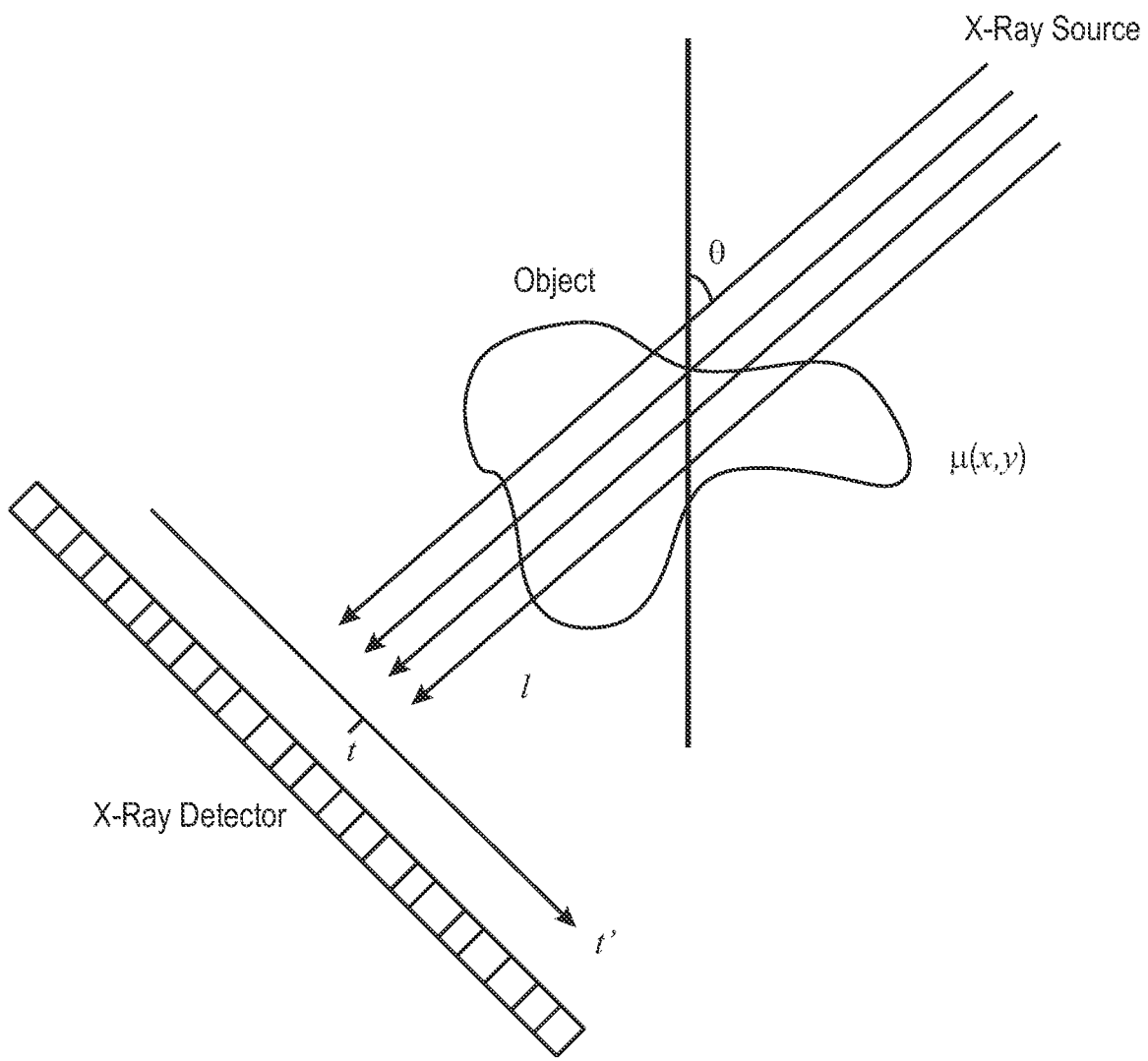

In an embodiment, the computer 50 also performs post-processing and image reconstruction of the image data output from the X-ray detector 20. The computer 50 thereby corresponds to the image processing system 30 as shown in FIGS. 1 and 2. The associated display 62 allows the operator to observe the reconstructed images and other data from the computer 50.

The X-ray source 10 arranged in the gantry 11 emits X-rays. An X-ray detector 20, which may be in the form of a photon-counting X-ray detector, detects the X-rays after they have passed through the object or patient. The X-ray detector 20 may for example be formed by plurality of pixels, also referred to as sensors or detector elements, and associated processing circuitry, such as Application Specific Integrated Circuits (ASICs), arranged in detector modules. A portion of the analog processing part may be implemented in the pixels, whereas any remaining processing part is implemented in, for instance, the ASICs. In an embodiment, the processing circuitry (ASICs) digitizes the analog signals from the pixels. The processing circuitry (ASICs) may also comprise a digital processing part, which may carry out further processing operations on the measured data, such as applying corrections, storing it temporarily, and/or filtering. During a scan to acquire X-ray projection data, the gantry and the components mounted thereon rotate about an iso-center 13.

Modern X-ray detectors normally need to convert the incident X-rays into electrons, this typically takes place through the photoelectric effect or through Compton interaction and the resulting electrons are usually creating secondary visible light until its energy is lost and this light is in turn detected by a photo-sensitive material. There are also detectors, which are based on semiconductors and in this case the electrons created by the X-ray are creating electric charge in terms of electron-hole pairs which are collected through an applied electric field.

There are detectors operating in an energy integrating mode in the sense that they provide an integrated signal from a multitude of X-rays. The output signal is proportional to the total energy deposited by the detected X-rays.

X-ray detectors with photon counting and energy resolving capabilities are becoming common for medical X-ray applications. The photon counting detectors have an advantage since in principle the energy for each X-ray can be measured which yields additional information about the composition of the object. This information can be used to increase the image quality and/or to decrease the radiation dose.

Generally, a photon-counting X-ray detector determines the energy of a photon by comparing the height of the electric pulse generated by a photon interaction in the detector material to a set of comparator voltages. These comparator voltages are also referred to as energy thresholds. Generally, the analog voltage in a comparator is set by a digital-to-analog converter (DAC). The DAC converts a digital setting sent by a controller to an analog voltage with respect to which the heights of the photon pulses can be compared.

A photon-counting detector counts the number of photons that have interacted in the detector during a measurement time. A new photon is generally identified by the fact that the height of the electric pulse exceeds the comparator voltage of at least one comparator. When a photon is identified, the event is stored by incrementing a digital counter associated with the channel.

When using several different threshold values, a so-called energy-discriminating photon-counting detector is obtained, in which the detected photons can be sorted into energy bins corresponding to the various threshold values. Sometimes, this type of photon-counting detector is also referred to as a multi-bin detector. In general, the energy information allows for new kinds of images to be created, where new information is available and image artifacts inherent to conventional technology can be removed. In other words, for an energy-discriminating photon-counting detector, the pulse heights are compared to a number of programmable thresholds (Ti-TN) in the comparators and are classified according to pulse-height, which in turn is proportional to energy. In other words, a photon counting detector comprising more than one comparator is here referred to as a multi-bin photon counting detector. In the case of multi-bin photon counting detector, the photon counts are stored in a set of counters, typically one for each energy threshold. For example, counters can be assigned to correspond to the highest energy threshold that the photon pulse has exceeded. In another example, counters keep track of the number of times that the photon pulse cross each energy threshold.

As an example, edge-on is a special, non-limiting design for a photon-counting detector, where the X-ray sensors such as X-ray detector elements or pixels are oriented edge-on to incoming X-rays.

For example, such photon-counting detectors may have pixels in at least two directions, wherein one of the directions of the edge-on photon-counting detector has a component in the direction of the X-rays. Such an edge-on photon-counting detector is sometimes referred to as a depth-segmented photon-counting detector, having two or more depth segments of pixels in the direction of the incoming X-rays.

Alternatively, the pixels may be arranged as an array (non-depth-segmented) in a direction substantially orthogonal to the direction of the incident x-rays, and each of the pixels may be oriented edge-on to the incident x-rays. In other words, the photon-counting detector may be non-depth-segmented, while still arranged edge-on to the incoming X-rays.

By arranging the edge-on photon-counting detector edge-on, the absorption efficiency can be increased, in which case the absorption depth can be chosen to any length, and the edge-on photon-counting detector can still be fully depleted without going to very high voltages.

A conventional mechanism to detect X-ray photons through a direct semiconductor detector basically works as follows. The energy of the X-ray interactions in the detector material are converted to electron-hole pairs inside the semiconductor detector, where the number of electron-hole pairs is generally proportional to the photon energy. The electrons and holes are drifted towards the detector electrodes and backside (or vice versa). During this drift, the electrons and holes induce an electrical current in the electrode, a current which may be measured.

Figure 4:
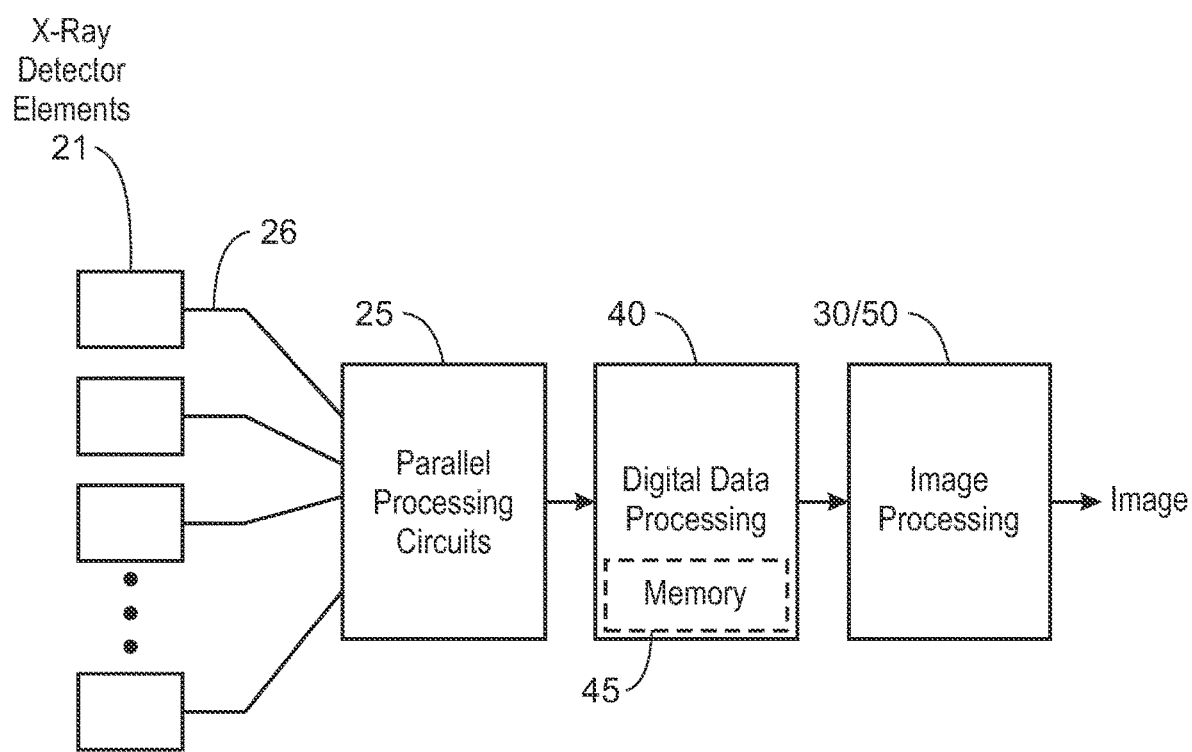
FIG. 4 is a schematic diagram illustrating another example of relevant parts of an x-ray imaging system, such as a CT imaging system.

As illustrated in FIG. 4, signal(s) is/are routed 26 from detector elements 22 of the X-ray detector to inputs of parallel processing circuits (e.g., ASICs) 25. It should be understood that the term Application Specific Integrated Circuit (ASIC) is to be interpreted broadly as any general circuit used and configured for a specific application. The ASIC processes the electric charge generated from each X-ray and converts it to digital data, which can be used to obtain measurement data such as a photon count and/or estimated energy. The ASICs are configured for connection to digital data processing circuitry so the digital data may be sent to further digital data processing 40 and/or one or more memory circuits or components 45 and finally the data will be the input for image processing 30/50 to generate a reconstructed image.

As the number of electrons and holes from one x-ray event is proportional to the energy of the X-ray photon, the total charge in one induced current pulse is proportional to this energy. After a filtering step in the ASIC, the pulse amplitude is proportional to the total charge in the current pulse, and therefore proportional to the X-ray energy. The pulse amplitude can then be measured by comparing its value with one or more thresholds (THR) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value (THR) which has been detected within a certain time frame.

The ASIC typically samples the analog photon pulse once every Clock Cycle and registers the output of the comparators. The comparator(s) (threshold) outputs a one or a zero depending on whether the analog signal was above or below the comparator voltage. The available information at each sample is, for example, a one or a zero for each comparator representing weather the comparator has been triggered (photon pulse was higher than the threshold) or not.

In a photon counting detector, there is typically a Photon Counting Logic which determines if a new photon has been registered and, registers the photons in counter(s). In the case of a multi-bin photon counting detector, there are typically several counters, for example one for each comparator, and the photon counts are registered in the counters in accordance with an estimate of the photon energy. The logic can be implemented in several different ways. Two of the most common categories of Photon Counting Logic are the so-called non-paralyzable counting modes, and the paralyzable counting modes. Other photon-counting logics include, for example, local maxima detection, which counts, and possibly also registers the pulse height of, detected local maxima in the voltage pulse.

There are many benefits of photon-counting detectors including, but not limited to: high spatial resolution; less sensitivity to electronic noise; good energy resolution: and material separation capability (spectral imaging ability). However, energy integrating detectors have the advantage of high count-rate tolerance. The count-rate tolerance comes from the fact/recognition that, since the total energy of the photons is measured, adding one additional photon will always increase the output signal (within reasonable limits), regardless of the amount of photons that are currently being registered by the detector. This advantage is one of the main reasons that energy integrating detectors are the standard for medical CT today.

Figure 5:
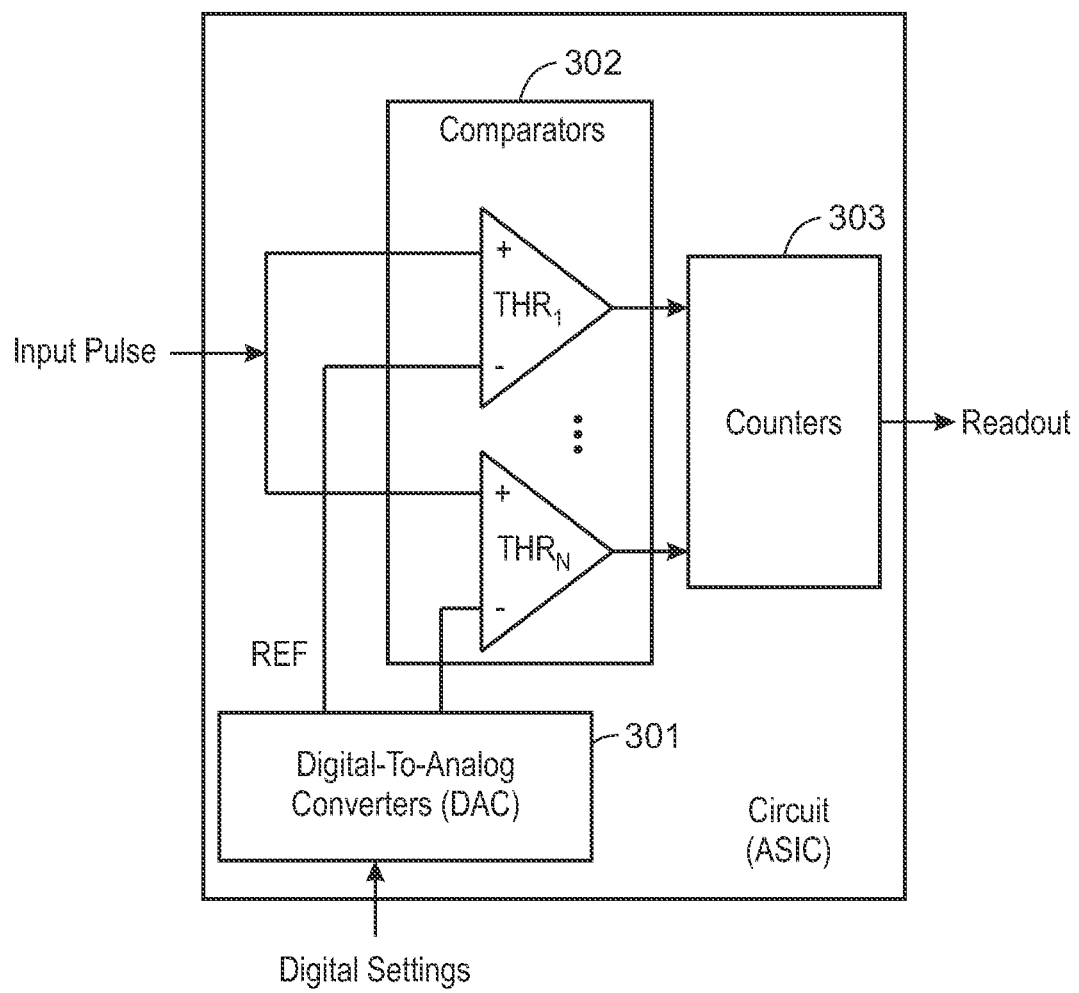
FIG. 5 is a schematic illustration of a photon-counting circuit and/or device according to prior art.

FIG. 5 shows a schematic illustration of a photon-counting circuit and/or device according to prior art.

When a photon interacts in a semiconductor material, a cloud of electron-hole pairs is created. By applying an electric field over the detector material, the charge carriers are collected by electrodes attached to the detector material. The signal is routed from the detector elements to inputs of parallel processing circuits, e.g., ASICs. It should be understood that the term Application Specific Integrated Circuit, ASIC, is to be interpreted broadly as any general circuit used and configured for a specific application. The ASIC processes the electric charge generated from each X-ray and converts it to digital data, which can be used to obtain measurement data such as a photon count and/or estimated energy. In one example, the ASIC can process the electric charge such that a voltage pulse is produced with maximum height proportional to the amount of energy deposited by the photon in the detector material.

The ASIC may include a set of comparators 302 where each comparator 302 compares the magnitude of the voltage pulse to a reference voltage. The comparator output is typically zero or one (0/1) depending on which of the two compared voltages that is larger. Here we will assume that the comparator output is one (1) if the voltage pulse is higher than the reference voltage, and zero (0) if the reference voltage is higher than the voltage pulse. Digital-to-analog converters (DACs), 301 can be used to convert digital settings, which may be supplied by the user or a control program, to reference voltages that can be used by the comparators 302. If the height of the voltage pulse exceeds the reference voltage of a specific comparator, we will refer to the comparator as triggered. Each comparator is generally associated with a digital counter 303, which is incremented based on the comparator output in accordance with the photon counting logic.

As previously mentioned, when the resulting estimated basis coefficient line integral $\hat{A}_i$, for each projection line is arranged into an image matrix, the result is a material specific projection image, also called a basis image, for each basis i. This basis image can either be viewed directly (e.g., in projection x-ray imaging) or taken as input to a reconstruction algorithm to form maps of basis coefficients $\alpha_1$ inside the object (e.g., in CT). Anyway, the result of a basis decomposition can be regarded as one or more basis image representations, such as the basis coefficient line integrals or the basis coefficients themselves.

It will be appreciated that the mechanisms and arrangements described herein can be implemented, combined and re-arranged in a variety of ways.

For example, embodiments may be implemented in hardware, or at least partly in software for execution by suitable processing circuitry, or a combination thereof.

The steps, functions, procedures, and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, and/or blocks described herein may be implemented in software such as a computer program for execution by suitable processing circuitry such as one or more processors or processing units.

In the following, non-limiting examples of specific detector module implementations will be discussed. More particularly, these examples refer to edge-on oriented detector modules and depth-segmented detector modules. Other types of detectors and detector modules may also be feasible.

Figure 6:
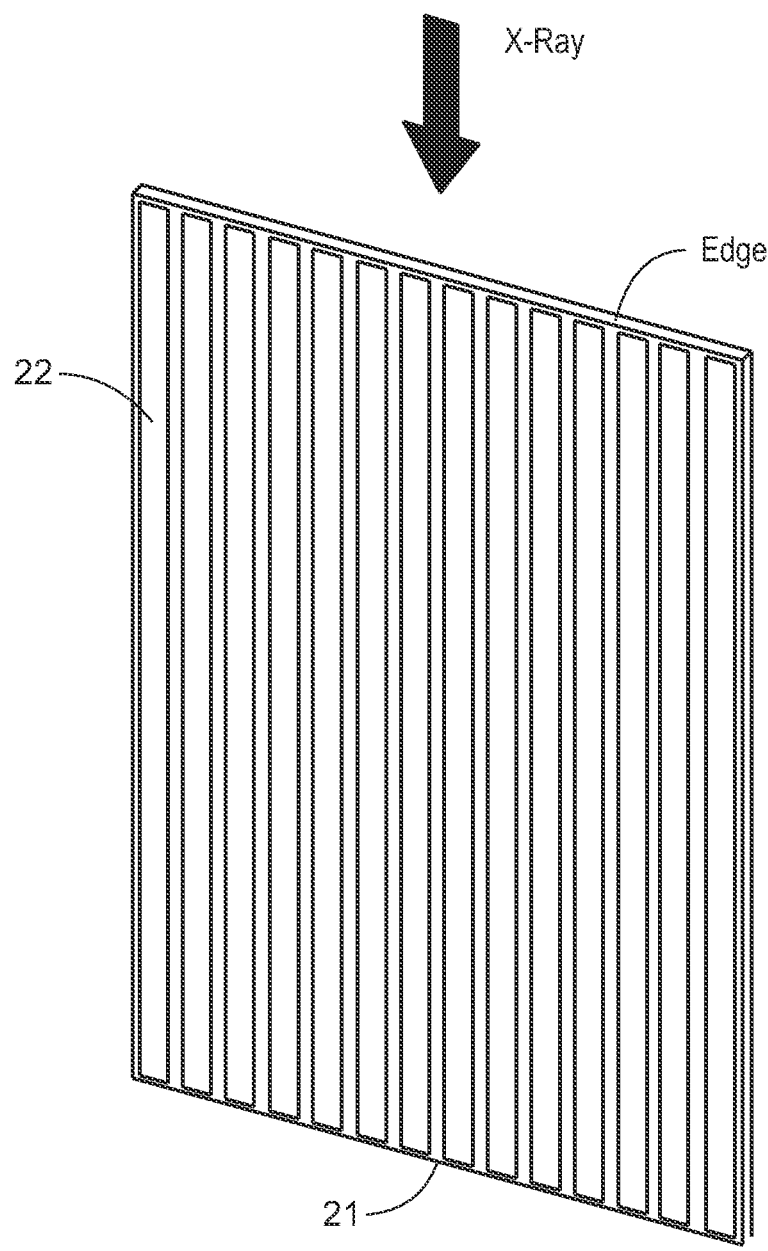
FIG. 6 is a schematic diagram illustrating an example of a semiconductor detector sub-module according to an exemplary embodiment.

FIG. 6 is a schematic diagram illustrating an example of a semiconductor detector sub-module according to an exemplary embodiment. This is an example of a semiconductor detector sub-module with the semiconductor sensor 21 split into detector elements or pixels 22, where each detector element (or pixel) is normally based on a diode having a charge collecting electrode as a key component. The X-rays enter through the edge of the semiconductor sensor.

Figure 7:
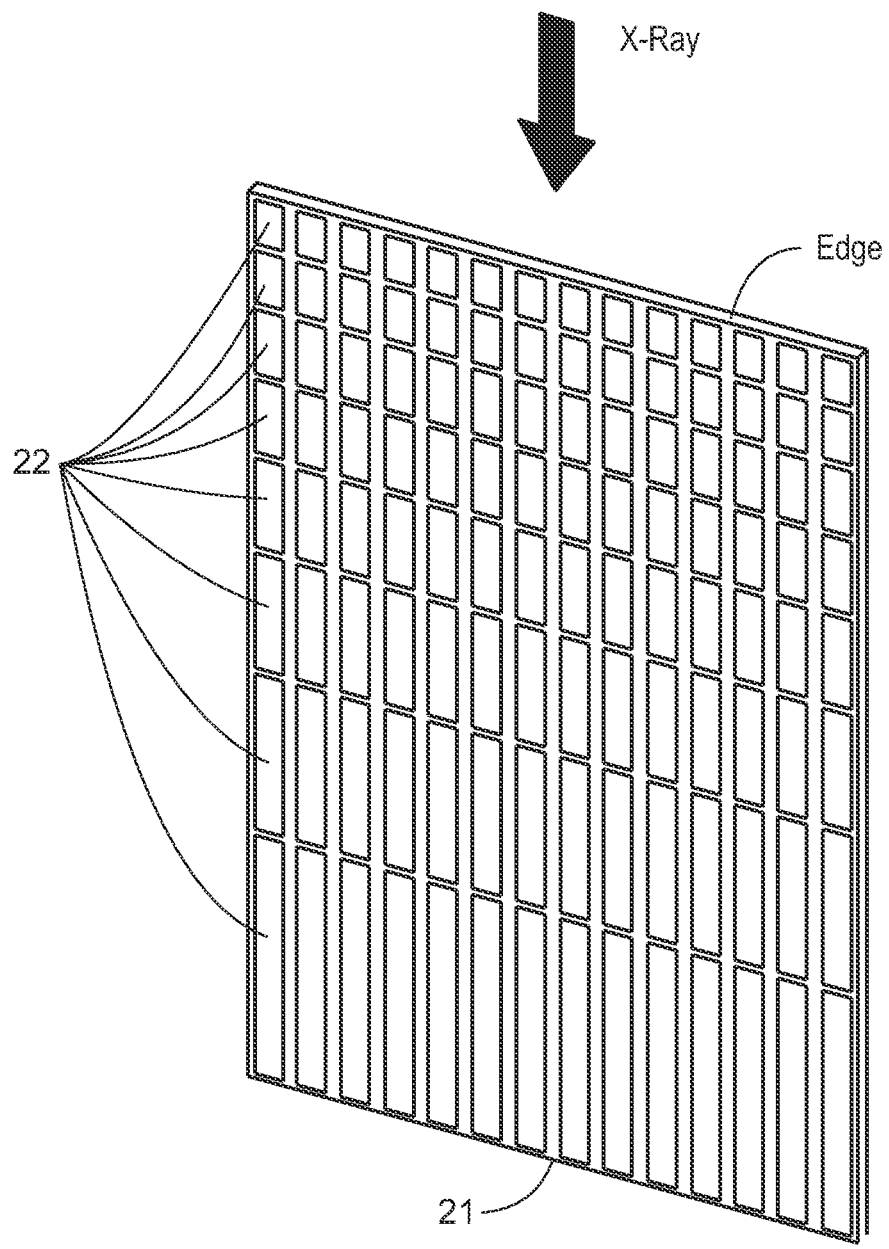
FIG. 7 is a schematic diagram illustrating an example of semiconductor detector sub-module according to another exemplary embodiment.

FIG. 7 is a schematic diagram illustrating an example of semiconductor detector sub-module according to another exemplary embodiment. In this example, the semiconductor sensor 21 is also split into a plurality of so-called depth segments or detector elements 22 in the depth direction, again assuming the X-rays enter through the edge.

Normally, a detector element is an individual X-ray sensitive sub-element of the detector. In general, the photon interaction takes place in a detector element and the thus generated charge is collected by the corresponding electrode of the detector element.

Each detector element typically measures the incident X-ray flux as a sequence of frames. A frame is the measured data during a specified time interval, called frame time.

Depending on the detector topology, a detector element may correspond to a pixel, especially when the detector is a flat-panel detector. A depth-segmented detector may be regarded as having a number of detector strips, each strip having a number of depth segments. For such a depth-segmented detector, each depth segment may be regarded as an individual detector element, especially if each of the depth segments is associated with its own individual charge collecting electrode.

The detector strips of a depth-segmented detector nonnally correspond to the pixels of an ordinary flat-panel detector, and therefore sometimes also referred to as pixel strips. However, it is also possible to regard a depth-segmented detector as a three-dimensional pixel array, where each pixel (sometimes referred to as a voxel) corresponds to an individual depth segment/detector element.

The semiconductor sensors may be implemented as so called Multi-Chip Modules (MCMs) in the sense that the semiconductor sensors are used as base substrates for electric routing and for a number of ASICs which are attached preferably through so called flip-chip technique. The routing will include a connection for the signal from each pixel or detector element to the ASIC input as well as connections from the ASIC to external memory and/or digital data processing. Power to the ASICs may be provided through similar routing taking into account the increase in cross-section which is required for the large currents in these connections, but the power may also be provided through a separate connection. The ASICS may be positioned on the side of the active sensor and this means it can be protected from the incident X-rays if an absorbing cover is placed on top and it can also be protected from scattered X-rays from the side by positioning an absorber also in this direction.

Figure 8B:
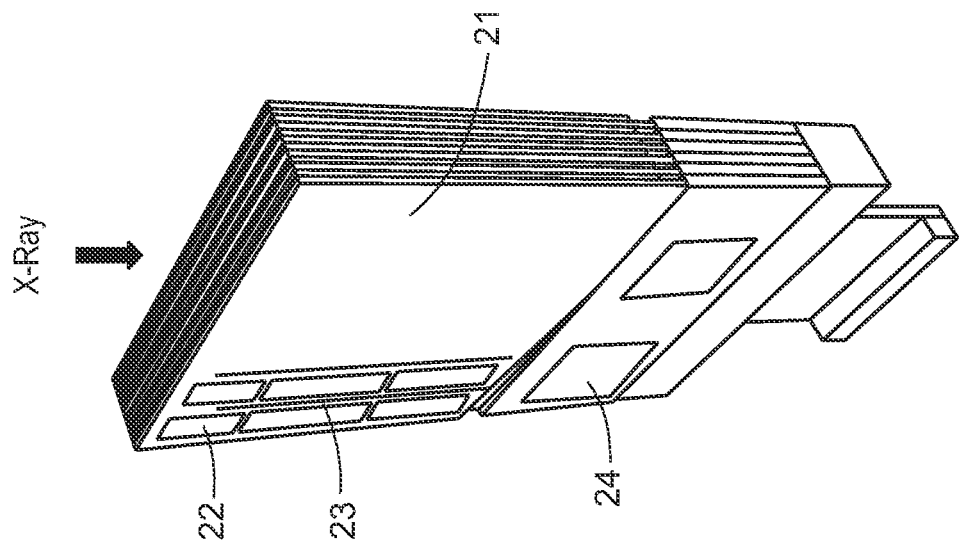
FIG. 8B is a schematic diagram illustrating an example of a set of tiled detector sub-modules, where each detector sub-module is a depth-segmented detector sub-module and the Application Specific Integrated Circuits (ASICs) or corresponding circuitry are arranged below the detector elements as seen from the direction of the incoming X-rays.
Figure 8A:
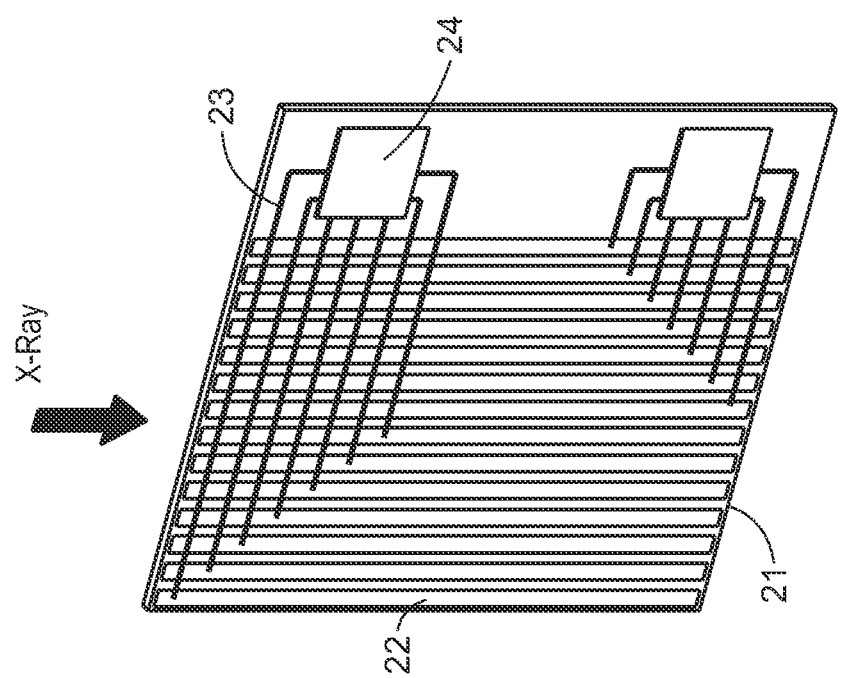
FIG. 8A is a schematic diagram illustrating an example of a semiconductor detector sub-module according to yet another exemplary embodiment.

FIG. 8A is a schematic diagram illustrating a semiconductor detector sub-module implemented as a MCM similar to embodiments in U.S. Pat. No. 8,183,535. In this example, it is illustrated how the semiconductor sensor 21 also can have the function of substrate in a MCM. The signal is routed by signal paths 23 from the detector elements or pixels 22 to inputs of parallel processing circuits 24 (e.g., ASICs) that are positioned next to the active sensor area. It should be understood that the term Application Specific Integrated Circuit (ASIC) is to be interpreted broadly as any general integrated circuit used and configured for a specific application. The ASICs process the electric charge generated from each X-ray and converts it to digital data which can be used to detect a photon and/or estimate the energy of the photon. The ASICs may have their own digital processing circuitry and memory for small tasks. And, the ASICs may be configured for connection to digital processing circuitry and/or memory circuits or components located outside of the MCM and finally the data will be used as input for reconstructing an image.

However, the employment of depth segments also brings two noticeable challenges to a silicon-based photon-counting detector. First, a large number of ASIC channels has to be employed to process data fed from the associated detector segments. In addition to the increased number of channels due to both the smaller pixel size and the depth segmentation, multi-energy bin further increases the data size. Second, since the given X-ray input counts are divided into smaller pixels, segments and energy bins, each bin has much lower signal and so the detector calibration/correction requires more than several orders of magnitude more calibration data to minimize statistical uncertainty.

Naturally, the several orders of magnitude larger data size slow down both data handling and pre-processing in addition to the need of larger computing resources, harddisk, memory and central processing unit (CPU)/graphics processing unit (GPU). When the size of data is 10 Gigabytes instead of 10 Megabyte, for example, the data handling time, read and write, can take 1000 times longer. For pileup (Radiation Detection and Measurement, Glenn F. Knoll., $3^{rd}$ edition., John Wiley & Sons Inc, pp. 632-pp. 642) calibration vector generation, the pileup calibration data needs to be pre-processed for spit correction. For material decomposition vector generation, the material decomposition data needs to be pre-processed for both spit and pileup correction. For patient scan data, the data needs to be pre-processed for spit, pileup and material decomposition before the image reconstruction gets started. These are simplified examples to explain "pre-processing" since the actual pre-processing steps can include several other calibration steps as needed, like reference normalization and air calibration. The term "processing" may indicate only the final step in each calibration vector generation or patient scan, but it is used interchangeably in some cases.

FIG. 8B is a schematic diagram illustrating an example of a set of tiled detector sub-modules, where each detector sub-module is a depth-segmented detector sub-module and the ASICs or corresponding circuitry 24 are arranged below the detector elements 22 as seen from the direction of the incoming X-rays, allowing for routing paths from the detector elements 22 to the ASICs 23 in the space between detector elements.

The present invention relates to a system architecture for an improved data handling capability with respect to data processing and/or data transferring.

According to a first aspect there is provided a CT imaging system comprising a gantry including a rotating member on a rotating side and a stationary member on a stationary side. The rotating member on the rotating side comprises an X-ray source configured to emit X-rays, an X-ray detector configured to generate detector data, a data storage unit configured to store the detector data, and processing circuitry configured to process at least part of the stored detector data to generate a processed data set. The stationary member on the stationary side is communicatively coupled to the rotating member on the rotating side. The CT imaging system further comprises a data communication system configured to transfer the processed data set from the rotating member on the rotating side to the stationary member on the stationary side.

By way of example, the rotating member may be a rotating part/section/segment/portion, of the gantry, which is configured to rotate, e.g. around the subject/object to be imaged. The stationary member may be defined as a stationary part/section/segment/portion, of the gantry, which is arranged in a stationary manner on the stationary side, wherein the rotating and stationary member may be communicatively connected via a data communication system. e.g. a slip ring.

By storing data on a rotating side of a CT imaging system, processing at least a part of the data to generate a processed data set on the rotating side and transferring or sending the processed data set to the stationary side, it is possible to get relevant data at the stationary side in a fast, efficient and versatile manner. Processing at least part of the detector data on the rotating side may reduce the data size of the data being transferred via the data communication system, e.g. the slip ring, by factors of 2-20000×, making many calibration and/or imaging steps capable of sending the data within existing slip-ring bandwidth, thus speeding up the overall process of imaging and/or calibrating. The data storage unit may comprise a dedicated large memory, for example, non-volatile memory express (NVMe). The data storage unit on the rotating side may comprise, in addition or alternatively, a temporary memory needed during a continuous data processing, for example, ASIC, field-programmable gate array (FPGA) register or memory. The data storage unit may comprise, in addition or alternatively, a RAM (random access memory). The processing of the data stored on the rotating side may include one or more operations. As an example, an operation may be for example, but not limited to, X-ray source or X-ray tube spit correction, data accumulation, and pileup correction.

An X-ray tube "spit" refers to a temporary electrical short-circuit that sometimes occurs inside an X-ray tube. Typically, upon the occurrence of tube-spit, the supply of power to the X-ray tube is temporarily blocked to prevent arching and generates no X-ray output. A spit can be corrected and is currently applied at the stationary side, see U.S. Pat. No. 7,114,850. When the correction is done at the rotating side, it enables frame accumulation for detector data, e.g., calibration data, at the rotating side as well. As mentioned, with a given X-ray input, smaller pixel, depth segments and multi-energy bins reduce X-ray count in each bin by an order of magnitude (input X-ray counts/(pixel size ratio ×number of segments ×number of energy bins)). To generate a statistically meaningful calibration vectors, for example, pileup (each X-ray hit generates a certain length of electrical signal. Due to the finite length of the signal pulse, it can overlap with the next incoming X-ray pulses. The overlap is called "pileup". It distorts both counts and energy distribution that needs to be corrected.) and materia decomposition requires many frames, 100-10000, accumulated or averaged. Due to the large amount of the data size, even with the latest computing power at the stationary side, rather simple spit and accumulation tasks take a while that is impractical. The distributed electronics at the rotating side. ASIC/FPGA/CPU (40/45 in FIG. 4, 114/118/116 in FIG. 9) per subdetector, can parallelly be utilized to achieve the same goal without any delay or within unnoticeable time.

When the frames are accumulated, the data size is smaller which enables both quick data transfer though the data communication system, e.g., a slip ring, and faster processing of the detector data, e.g., calibration data, to generate pileup and material decomposition calibration vectors at the stationary side.

In addition, to make the data acquisition more efficient, pileup and material decomposition calibration vectors/algorithms can be loaded into a register/memory, e.g., the data storage unit, and concurrently applied to the data being collected. It eliminates the slower stationary side calibration pre-processing by utilizing the parallel detector electronics.

Once the data are corrected at the rotating side, pixels and segments can be combined to support different patient scan modes, for example, ultra-high resolution, high resolution, cardiac specific, axial scan, etc. One example patient scan mode requires ultra-high spatial resolution, another exemplary scan mode requires better material contrast that can be achieved by combining pixels to increase statistics. The combined data can be promptly transferred to the stationary side and reconstructed for patient diagnosis.

As an example, X-ray tube spit correction may be implemented as follows. While reading out one frame of the ASIC energy bin counts to an ASIC register/memory, the X-ray tube spit information for the frame gets broadcasted to all detector elements through a data acquisition board. The length of one frame is typically longer than 25 µsec to accumulate X-ray counts, and the spit broadcasting from an X-ray tube can be done in less than 1 µsec. During the time of the next frame collection, if a spit occurred in the current frame, a spit correction is applied to the current frame and the corrected current frame is moved to the next register/memory in ASIC. This allows the first register/memory space to be used for the next frame while the spit correction is applied seamlessly.

The spit corrected views can be accumulated as needed. As an exemplary, if 1000 frames are to be accumulated, the count from each frame may be summed. After the 1000th frame, the summed count gets transferred to the data communication unit, e.g., 130-1 in FIG. 9, and the register/memory gets reset for the next 1000 frames.

Since the modern FPGA has a great amount of computing resources, a processing circuitry can be implemented in FPGA to execute more complex algorithm. A simple example is to do view averaging and standard deviation calculation. A more complex algorithm will be applying a pileup algorithm to the data stream.

For example, the present system architectural invention allows data to be processed and transferred concurrently, which may speed up the process of using a CT imaging system and retrieving a result. The present invention may further speed up the process of retrieving a result, by allowing data to be promptly processed in the rotating side and turn them into a format which is faster and/or more efficient to transfer through the data communication system in terms of information sent per unit of time.

Furthermore, the present invention is advantageous in that it allows a CT imaging system to be more versatile with respect to selection of and timing of data for processing and transferring. In particular, by storing detector data in the data storage unit on the rotating side, without any pre-processing or compression, a CT imaging system with such improved versatility is achieved. For example, the system may be used in one way for a quick patient scan, and in another way for a more thorough examination of a subject/object, since it provides the option of choosing what data to process and send, and when. For the quick patient scan the system may process the detector data of a fill scan, by for example merging, with respect to view and/or pixels, on the rotating side, and transfer the processed data to the stationary side where e.g., the final steps of generating an image is performed. This allows a user of the CT imaging system to retrieve a good-enough result in a faster way. In the case of a thorough examination, the CT imaging system may transfer the full raw detector data as generated by the X-ray detector to the stationary side.

According to an embodiment, the processed data set comprises a reduced data set. By the term "reduced data set" it is here meant, but not limited to, a data set resulting from operations on a previous data set, e.g., the generated detector data, which reduces the size of the data. As mentioned, due to small pixel, depth segment and energy bins, detector calibration requires multiple same view/frame data to reduce statistical error. Examples of operations being performed on the same view data include averaging data per each energy bin and/or accumulating frame data per each energy bin, wherein a detector element may comprise at least one energy bins. The input can be e.g., 1000 views and its output is one accumulated or averaged view. They can be achieved concurrently in ASIC while each view data was readout from the detector. Or the count can be transferred to a separate other memory and accumulated.

In the following, "output modes" of the processing circuitry will be described with reference to a number of optional features. It is to be understood that any combination of these features is envisioned by the inventors.

According to an embodiment, the processing circuitry is configured to operate in a plurality of output modes, each generating a respective processed data set. For example, the plurality of output modes may comprise an output mode for calibration and an output mode for patient imaging. The plurality of output modes may comprise a plurality of different calibration modes for a CT imaging system and a plurality of output modes for patient imaging.

The plurality of output modes may generate respective processed data sets, each being different from the other output modes with respect to the data size of the respective generated processed data set.

According to an embodiment, an output mode is selected in response to a request to generate a corresponding processed data set using the selected output mode. The present embodiment allows a user of the CT imaging system to request an output mode via a user interface. Hence, a user may at least partially decide how to run the CT imaging system, in terms of how data is handled. The user interface may be e.g., a display on a computer on the rotating side or the stationary side.

According to an embodiment, the processing circuitry is configured to select a pre-determined output mode to generate a corresponding processed data set using the pre-determined output mode, which allows a CT imaging system to run one or more output modes without the need for a user to request a certain output mode. For example, the CT imaging system may have one or more default modes that are predetermined.

According to an embodiment, the processing circuitry is configured to process the stored data using a set of consecutive output modes to generate respective processed data sets, and wherein the data communication system is configured to transfer the respective processed data sets consecutively. The present embodiment is advantageous in that the CT imaging system may operate in steps, wherein the steps may be predetermined. For example, this allows the CT imaging system to optimize how the detector data is stored, processed and transferred for first generating an initial image for quick diagnosis, followed by generating a more detailed image for final diagnosis. Furthermore, the present embodiment allows the CT imaging system to process and transfer one or more processed data sets without requiring input from a user, thus reducing downtime for the whole process by avoiding pauses between steps.

According to an embodiment, parts of a first processed data set is transferred via the data communication system, while other parts of the first processed data set is being generated, such that the processing of the detector data and the transferring of a processed data set from the rotating member on the rotating side to the stationary member on the stationary side is performed at least partially simultaneously. The present embodiment allows a CT imaging system to be used in a quicker and more efficient manner, essentially reducing the time it takes from performing the scan of the subject/object to producing an image reconstructed from the detector data.

According to an embodiment, the data communication system comprises a first data communication unit on the rotating member on the rotating side and a second data communication unit on the stationary member on the stationary side.

According to an embodiment, the data communication system comprises one or more slip rings.

According to an embodiment, the X-ray detector is configured to send the detector data to the data storage unit, and wherein the data storage unit is configured to store the generated detector data in its entirety. The present embodiment is advantageous in that all information from a scan using the CT imaging system is stored and can be processed or transferred, which allows a more versatile way to handle the detector data.

According to an embodiment, the data storage unit is a non-volatile memory, NVMe, and/or a Random Access Memory, RAM, which allows the CT imaging system to store detector data and/or processed data on the rotating side in order to optimize the data handling. The NVMe may provide more reliable storing of data, to e.g., minimize consequences due power loss.

According to an embodiment, the data storage unit is a set of transitory registers that is a part of the data processing circuitry.

According to an embodiment, the X-ray detector is a photon-counting detector. The present invention is especially useflul for detector technologies which generate large amounts of data, such as photon-counting detectors.

According to an embodiment, the X-ray detector is an energy-discriminating detector, such as a detector with multiple energy bins.

According to an embodiment, the processing of the detector data, to generate a processed data set, comprises combining detector data.

According to an embodiment, the processing circuitry is configured to process at least part of the generated detector data before it is stored on the data storage unit, in order to fuither optimize the data handling. Spit correction or pileup correction or other correction can be applied before the storage. After the storage, it can be transferred through the data communication unit, e.g., a slip ring, as it is, or segments, pixels and views can be combined depending on the patient data prescription. A filtering can be applied as well to smooth statistical variation.

According to an embodiment, the system comprises a second data storage unit, wherein the second data storage unit is configured to receive the processed data set from the rotating member on the rotating side, and a second set of processing circuitry, wherein the second set of processing circuitry is configured to process the received processed data set, wherein both the second data storage unit and the second set of processing circuitry are arranged on the stationary member on the stationary side.

For a better understanding, the proposed technology will now be described in further detail with reference to FIGS. 9-13 illustrating non-limiting examples of the data processing and transferring according to the invention.

Figure 9:
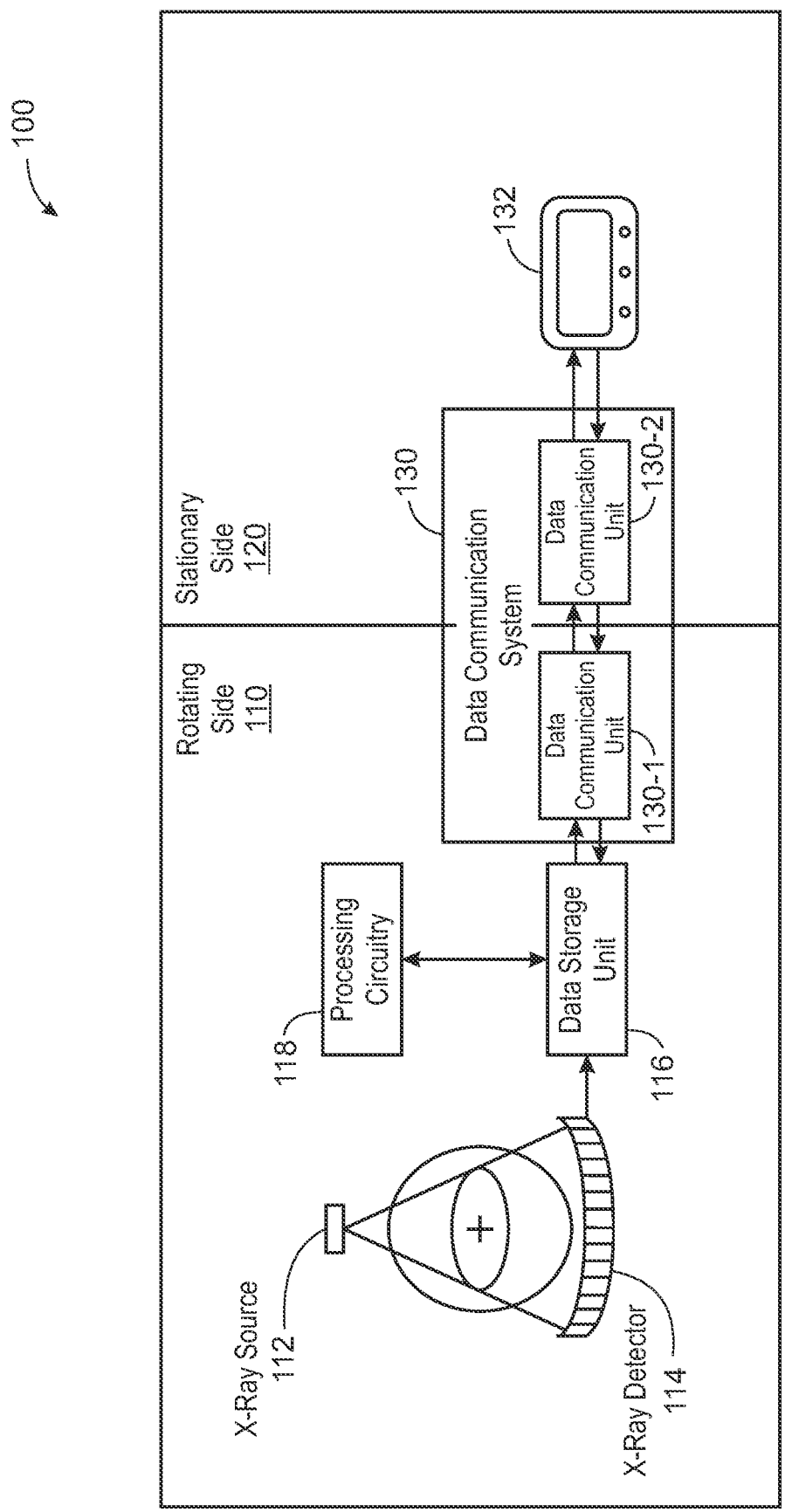
FIG. 9 schematically shows a CT imaging system 100 according to exemplifying embodiments.

FIG. 9 schematically shows a CT imaging system 100 according to an exemplifying embodiment of the present invention. In FIG. 9 the CT imaging system 100 comprises a rotating side 110 and a stationary side 120. The rotating side 110 may comprise a gantry including a rotating member arranged on the rotating side 110 which is able to rotate around a subject/object, e.g., as described in FIG. 3, with an X-ray source 112 arranged on one side of the gantry and an X-ray detector 114 arranged on the opposite side, such that X-rays emitted by the X-ray source 112 may pass through the subject/object and be received/detected at the X-ray detector 114. The X-ray detector 114 may be a photon counting detector, and optionally also a detector with multiple energy bins that is energy-discriminating, e.g., as described in FIGS. 3-7, 8a, 8b. The X-ray detector may alternatively be an energy-integrating detector (EID) in which the detected signal is proportional to the total energy deposited by all photons without specific information about an individual photon or its energy. The CT imaging system 100 further comprises a data storage unit 116, which allows detector data from the X-ray detector 114 to be stored on the rotating side 110. The data storage unit 116 may be a non-volatile memory. The CT imaging system 100 further comprises processing circuitry 118 which may receive data, such as detector data, and process it. By the term "processing circuitry" it is here meant circuitry, e.g., a processor, that is capable of performing operations, such as mathematical operations, for processing/transforming data. The processing circuitry may be digital processing circuitry.

The processing circuitry 118 and data storage unit 116 may be communicatively connected, such that data may be transferred between them. It is to be understood that the processing circuitry 118 may process detector data and/or already processed data, in order to get a resulting processed data set which may be transferred to the stationary side 120. The processed data set may be a reduced data set, wherein a reduced data set may have a reduced data size.

The processing performed by the processing circuitry 118 may comprise one or more operations, e.g., to change the format, or reduce the size, of the data. For example, at least parts of the detector data may be averaged or accumulated in order to generate a reduced data set with reduced data size. The reduction of data size may be performed through lossy and/or lossless compression. The CT imaging system 100 further comprises a data communication system 130, through which non processed detector data and/or processed detector data may be transferred from the rotating side 110 to e.g., a computer on the stationary side 120.

By way of example, the data communication system 130 may comprise a first data communication unit 130-1 on the rotating side and a second data communication unit 130-2 on the stationary side. For example, the data communication system 130 may be a slip ring typically used in CT imaging systems with a rotating member of a gantry. By "slip ring" it is here meant, but not limited to, an electromechanical device that allows the transmission of power and electrical signals, e.g., power and data transfer between a rotating structure and a stationary structure. The CT imaging system 100 of FIG. 9 may also comprise a display 132 coupled to the second data communication unit 130-2 and is configured to receive and display the processed data set.

Figure 10:
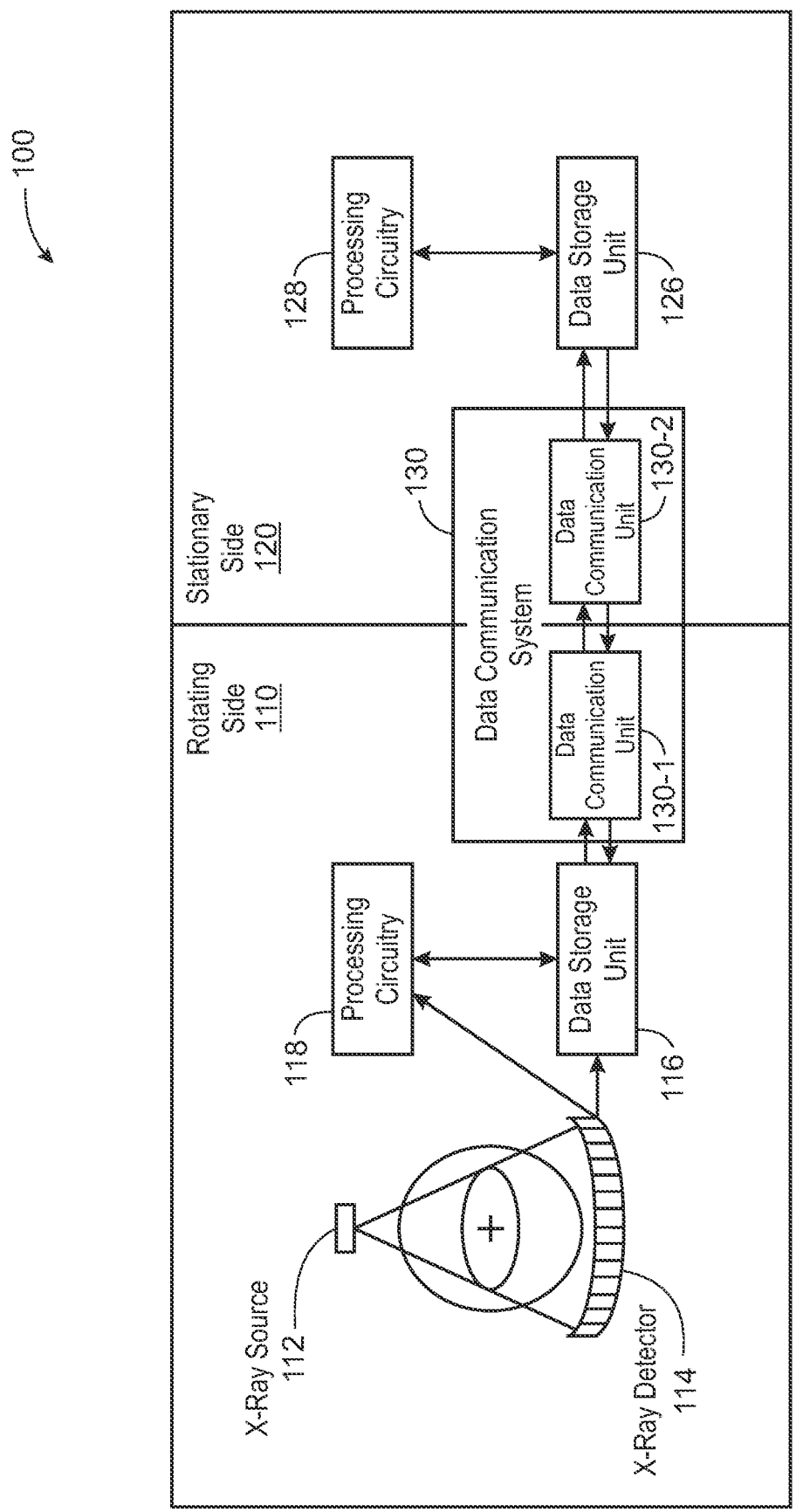
FIG. 10 schematically shows a CT imaging system 100 according to exemplifying embodiments.

FIG. 10 schematically shows CT imaging system 100 which is similar to the CT imaging system 100 in FIG. 9. Since much of the configuration and operation of the CT imaging system 100 is substantially similar to that described in FIG. 9, a detailed description of features common to the embodiment illustrated in FIG. 9 has been omitted to avoid needless prolixity and for the sake of brevity and conciseness.

In FIG. 10 the CT imaging system 100 comprises a second data storage unit 126 and a second set of processing circuitry 128 arranged on the stationary side 120. The second data storage unit 126 is configured to receive the processed data set from the rotating side 110, via the data communication system 130. The second set of processing circuitry 120 may be configured to process the data received at the data storage unit 126, in order to construct a final image of the scan of the object/subject. By way of example, the CT imaging system 100 may store the detector data in full. The CT imaging system 100 may process part of the detector data stored on the data storage unit 116, on the rotating side 110, with the processing circuitry 118 in order to generate a processed data set. The CT imaging system may also process all of the stored detector data on the rotating side 110 in order to generate a processed data set. The detector data being processed may be a copy of the stored detector data and/or the processed data set may be a new data set generated from the detector data set, thus allowing the same detector data to be processed multiple times in different ways.

The CT imaging system 100 may transfer the processed data set and/or detector data to the stationary side 120, via the data communication system 130. The transferred processed data set and/or detector data may be received by the data storage unit 126 and stored therein. For example, any processed data set and/or detector data may be processed on the stationary side 120, in order to e.g., finalize image reconstruction of the detector data. Hence, detector data may be processed once on the rotating side 110 and generate a processed data set, then processing may be performed again on the processed data set on the stationary side 120. Furthermore, the detector data may be transferred, in full, from the rotating side 110 to the stationary side 120, even if a part of the detector data has been used to generate a processed data set which has already been transferred to the stationary side 120. This may be useful in the scenario when a processed data set, based on detector data from a patient scan, is desired in a quicker manner to allow for quicker diagnosis, and a more thorough investigation is desired afterwards, based on the detector data in full.

The CT imaging system 100 may store any part of the detector data and/or processed data on the data storage unit 116 and/or the second data storage unit 126.

Figure 11:
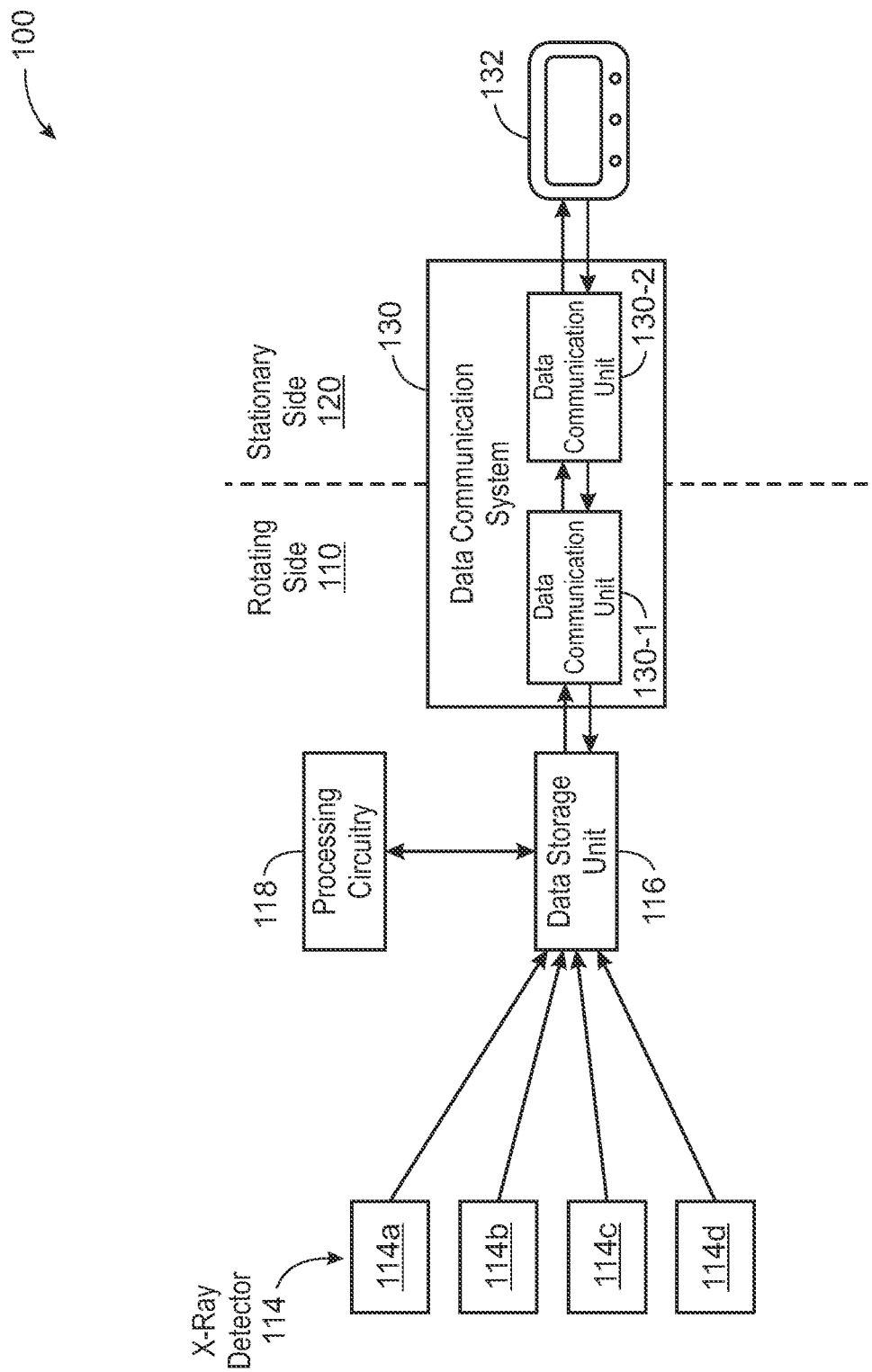
FIG. 11 schematically shows a CT imaging system 100 according to exemplifying embodiments.

FIG. 11 schematically shows CT imaging system 100 which is similar to the CT imaging system 100 in FIGS. 9 and 10. Because much of the configuration and operation of the CT imaging system 100 is substantially similar to that described in FIGS. 9 and 10, a detailed description of features common to the embodiment illustrated in FIGS. 9 and 10 has been omitted to avoid needless prolixity and for the sake of brevity and conciseness.

In FIG. 11 the X-ray detector 114 is an energy-discriminating detector comprising individual detector elements, 114a/114b/114c/114d. The CT imaging system 100 may discern the detector data coming from a specific detector element 114a/114b/114c/114d, store the detector data without losing the information on which detector element it originates from. The stored detector data may be processed by the processing circuitry 118, by performing one or more operations. For example, one operation may be that detector data from different detector elements 114a/114b/114c/114d are averaged, or that the data from certain elements, e.g., neighboring elements, are grouped together/accumulated. The CT imaging system provide the option of individually storing, processing and/or transferring, between the rotating side and the stationary side, detector data, and/or a processed data set from one or more detector elements 114a/114b/114c/114d. The CT imaging system 100 of FIG. 11 may also comprise a display 132 coupled to the second data communication unit 130-2 and is configured to receive and display the processed data set.

Figure 12:
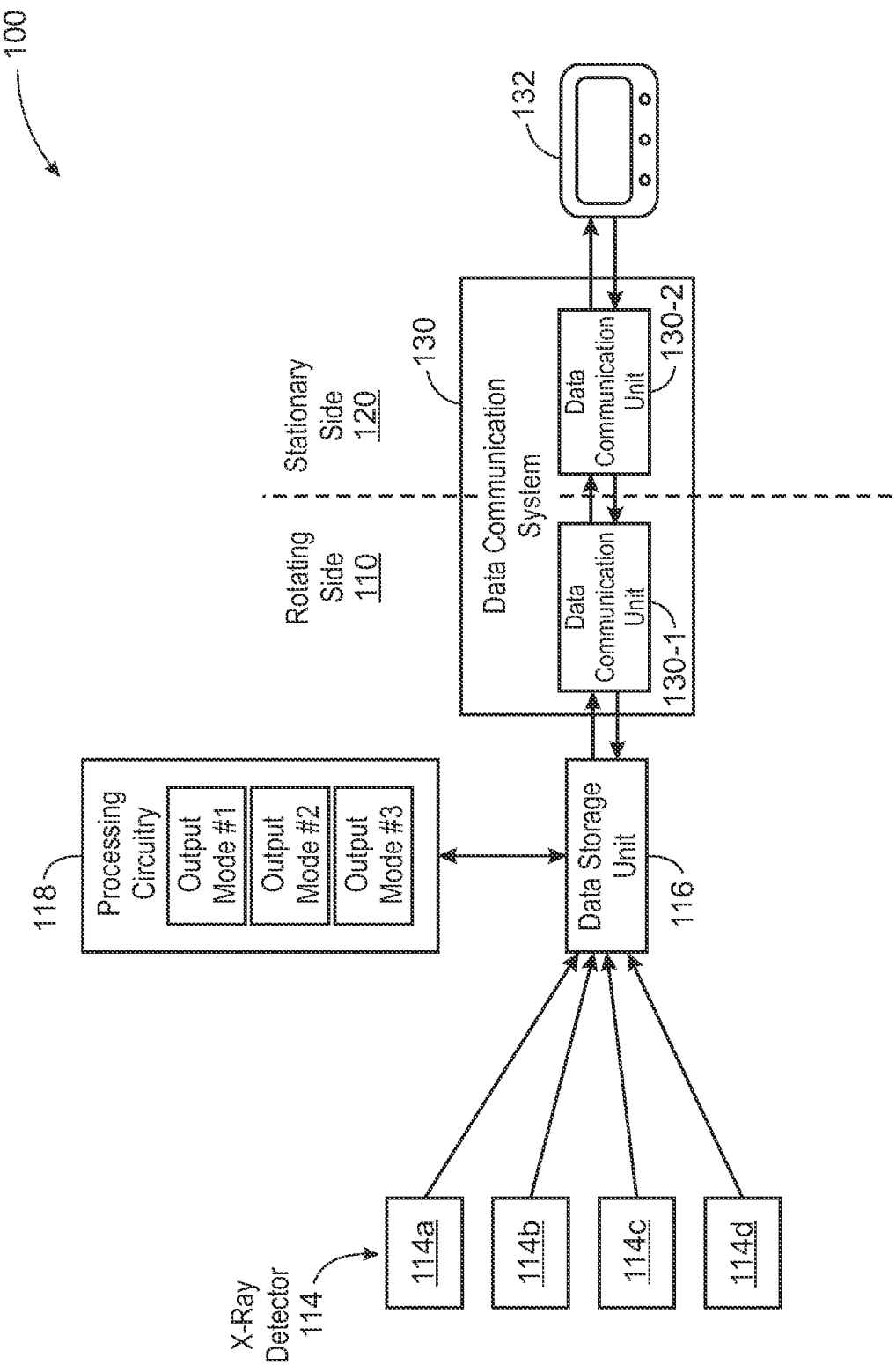
FIG. 12 schematically shows a CT imaging system 100 according to exemplifying embodiments.

FIG. 12 schematically shows CT imaging system 100 which is similar to the CT imaging system 100 in FIGS. 9, 10 and 11. Because much of the configuration and operation of the CT imaging system 100 is substantially similar to that described in FIGS. 9, 10 and 11, a detailed description of features common to the embodiment illustrated in FIGS. 9, 10 and 11 has been omitted to avoid needless prolixity and for the sake of brevity and conciseness.

In FIG. 12 the processing circuitry 118 is configured to operate in a plurality of output modes, wherein each output mode generates a respective processed data set. One or more output mode can be related to calibration of the CT imaging system 100, and one or more modes may be related to patient imaging. Calibrating a CT imaging system 100 may comprise producing correction coefficients used for the reconstruction of a later scan. A purpose of the calibration may be to characterize system-specific behavior which can be compensated for later, either before/during scanning or after scanning. The calibration may be performed by scanning phantoms, wherein the phantoms may be objects which imitates the human body in terms of composition, e.g., in order to provide references such that a more accurate quantitative representation of the scanned object/subject can be provided by the CT imaging system 100. Alternatively, calibration may be performed by scanning air, e.g., to normalize detector response at different locations in the detector. Another alternative is to calibrate by acquiring data with the X-ray source turned off, to e.g., characterize and compensate for phenomena due to detector electronics.

Calibration of the CT imaging system 100 may comprise taking multiple detector measurements to get multiple sets of detector data, and processing them together to compute the calibration coefficients. For instance, multiple consecutive scan/views, with corresponding detector data, taken at the same angle may be averaged together in order to reduce the influence of noise in the measurements and produce better statistics in the correction coefficients. One alternative is to transfer detector data to the stationary side 120 and perform the processing there; that could be quite slow when the bandwidth of the data communication system 130 is a bottleneck relative to the size of detector data. Another alternative is to generate one or more processed data sets on the rotating side 110 from the detector data, and transfer the processed data sets, which is smaller in data size than the detector data, which may allow faster transfer via the data communication system 130.

The CT imaging system 100 may provide the option of operating in many different patient imaging modes, such as a primary patient scan mode which allows the process of generating a reconstructed image to be faster but less detailed. The reason why the CT imaging system 100 may provide e.g., images faster is because the CT imaging system 100 allows specification of which detector data, stored on the data storage unit 116, that is to be processed by the processing circuitry 118, and also how the detector data is processed. Further, it allows a specified processed data set to be transferred to the stationary side 120 via the data communication system 130, allowing e.g., the most important/desired parts in the detector data to be processed and/or transferred to the stationary side 120 before the bulk of the detector data is processed and/or transferred. Another exemplary output mode is a secondary patient scan mode which provides more details in e.g., a reconstructed image, but takes longer to produce. The different output modes may be employed when scanning objects as well.

In a sense, an output mode may be regarded as a data processing mode in which a respective processed data set is generated and output for further use and/or transferring.

The respective processed data sets generated by a respective output mode may be different with respect to data size. For example, a first output mode may generate a first processed data set from a first part of the detector data, and a second output mode may generate a second processed data set from a second part of the detector data, wherein the first processed data set may be smaller in data size compared to the second processed data set. The detector data may be received from storage on the data storage unit 116, or be received directly from the X-ray detector 114, or from individual detector elements 114a/114b/114c/114d. The processing circuitry 118 may perform different operations on the data depending on what output mode is being run. The first part of the detector data may be the same as, or part of, the second part of the detector data. Depending on what output mode is being run, the amount of detector data being processed on the rotating side 110, and on the stationary side 120, may be altered, as well as at what point in time detector data and/or processed data sets are transferred to the stationary side 120.

The CT imaging system 100 may be configured, in e.g., the first output mode for patient imaging, to first produce a less detailed image based on the detector data from a scan of a subject/object, and afterwards produce a more detailed image of the scan. This may be done by initially generating the first processed data set from the first part of the detector data, followed by transferring the first processed data set via the data communication system 130 to the stationary side 120. Subsequently, the CT imaging system 100 may be configured, in the first output mode, to transfer the remaining detector data to the stationary side 120 via the data communication system 130, without processing it with the processing circuitry 118. The first output mode of the CT imaging system thus allows an initial, quicker, scan to be performed and shown to a user of the system, while the remaining detector data may be processed and/or transferred afterwards.

The CT imaging system 100 may be configured, in e.g., the second output mode, to initially process the second part of the detector data to generate the second processed data set, transfer the second processed data set via the data communication system 130, to the stationary side 120, to provide an image based on the second processed data set. Subsequently, the CT imaging system 100 may be configured to process a third part of the detector data to generate a third processed data set, which is then transferred via the data communication system 130, to the stationary side 120, in order to provide a secondary image with information not present in the second processed data set, e.g., to achieve a more detailed image. The CT imaging system 100 of FIG. 12 may also comprise a display 132 coupled to the second data communication unit 130-2 and is configured to receive and display the processed data set.

Figure 13:
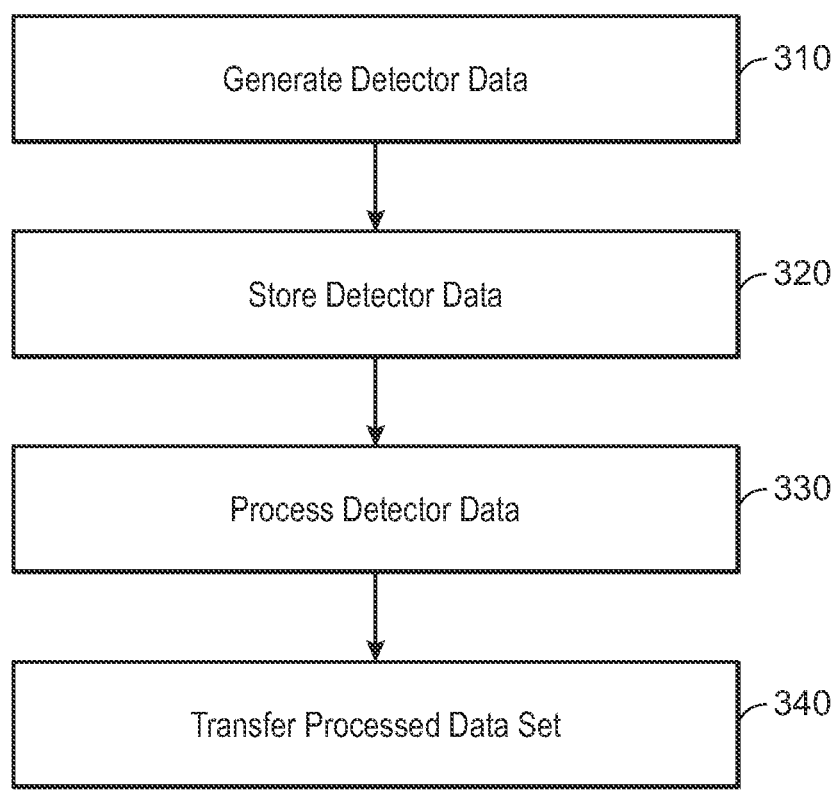
FIG. 13 is a schematic diagram illustrating an example of a method of operating a CT imaging system according to an embodiment.

FIG. 13 is a schematic diagram illustrating an example of a method of operating a CT imaging system according to an embodiment.

According to a second aspect there is provided a method of operating a CT imaging system. The CT imaging system comprises a rotating side comprising an X-ray source configured to emit X-rays, an X-ray detector, a data storage unit, processing circuitry and a stationary side communicatively coupled to the rotating side via a data communication system.

The method basically comprises generating 310 detector data via the X-ray detector and storing 320 the detector data in the data storage unit. The method further comprises processing 330 the stored detector data, in the processing circuitry, to generate a processed data set. The method further comprises transferring 340 the processed data set from the rotating side to the stationary side via the data communication system. "Storing data" may be done with a dedicated memory and/or a transit register/memory in a processing circuitry. For example, when the generating detector data 310 is concurrently processed through a transit register, 320 and 330 may be reversed or 320 may be skipped.

According to an embodiment, the processing, in the processing circuitry, comprises selecting an output mode out of a plurality of output modes, each generating a respective processed data set. The present embodiment is advantageous in that the CT imaging system is more versatile, since it can store and process data according to a need or desire of a user.

According to an embodiment, the processing, in the processing circuitry, comprises selecting an output mode out of a plurality of output modes, wherein each of the plurality of output modes generates a respective processed data set each being different from the others with respect to data size of the processed data set. The present embodiment is advantageous in that the data handling may be customized to fit different time frames and requirements on the resulting image.

According to an embodiment, an output mode out of a plurality of output modes in response to a request may be selected, to generate a corresponding processed data set using the selected output mode.

According to an embodiment, the transferring comprises transferring parts of a first processed data set via the data communication system, while other parts of the first processed data set is being generated, such that the processing of the detector data and the transferring of a processed data set from the rotating side to the stationary side is performed at least partially simultaneously.

According to an embodiment, the detector data is sent to the data storage unit, and wherein the data storage unit is configured to store the generated detector data in its entirety.

According to an embodiment, the processing circuitry is configured to process at least part of the generated detector data before it is stored on the data storage unit.

According to an embodiment, the processed data from the rotating side may be received, on the stationary side, at a second data storage unit, and the processed data received at the second data storage unit may be processed, on the stationary side, in a second set of processing circuitry.

Figure 14:
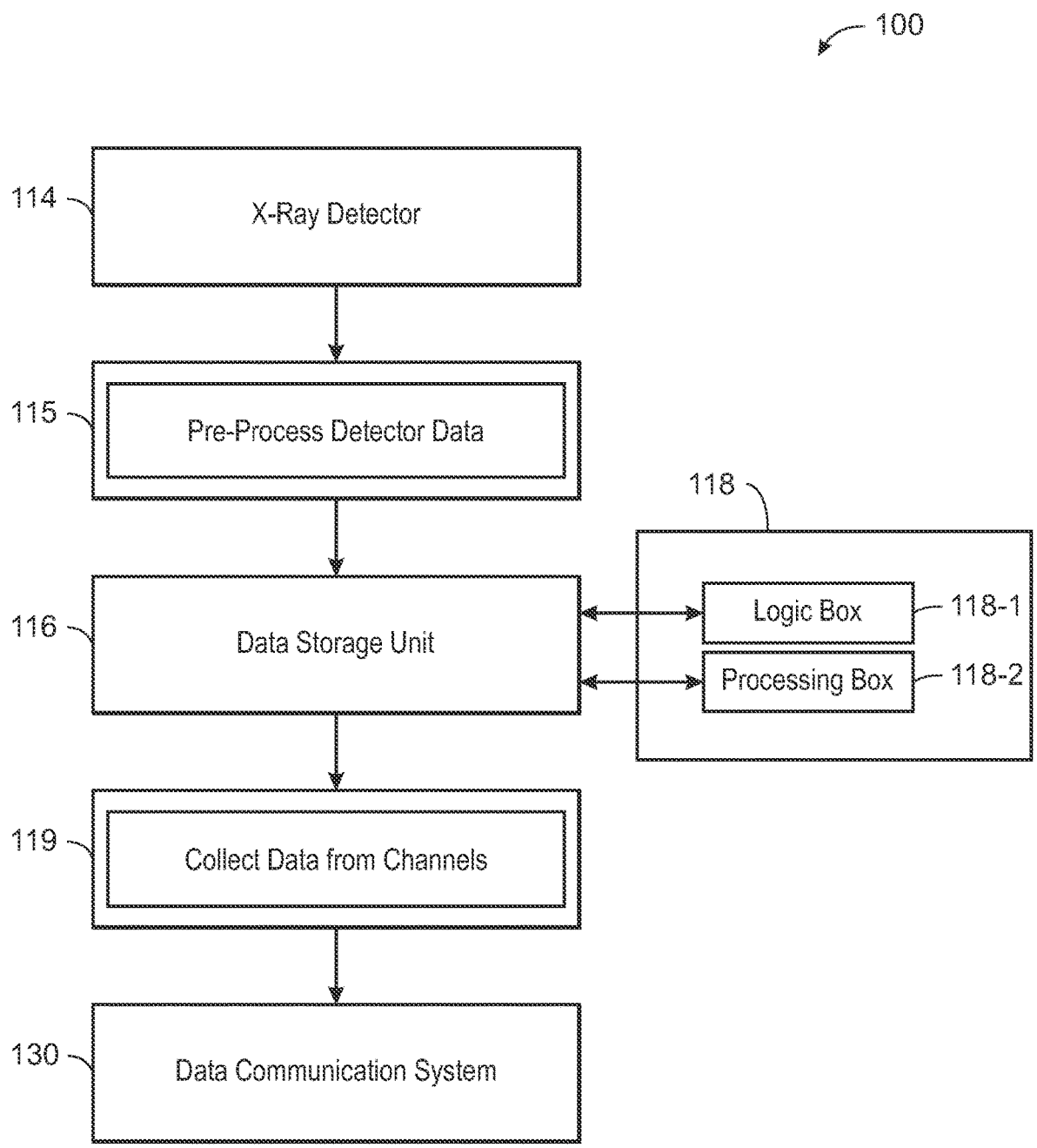
FIG. 14 is a schematic diagram illustrating an example of a method of operating a CT imaging system according to an embodiment.

FIG. 14 schematically shows a non-limiting example of a CT imaging system 100 according to an embodiment. In FIG. 14, the CT imaging system 100 comprises an X-ray detector 114, a data storage unit 116 and processing circuitry 118 arranged on the rotating side of the CT imaging system 100, e.g. on a rotating member of a gantry. Here, at least part of the generated detector data from the X-ray detector 114 is pre-processed by pre-processing circuitry 115 before being stored on the data storage unit 116 and/or before being processed by the processing circuitry 118. The processing circuitry 118 may comprise a logic box 118-1 and/or a processing box 118-2, wherein the processing box 118-2 may be configured to performer higher complexity computations compared to the logic box 118-1. The processing circuitry 118 may process at least part of the detector data on the data storage unit 116, and a data collector 119 may collect data, processed or non-processed, from all channels or a subset thereof and send it to the data communication system 130 which may then transfer the data from the rotating member of the gantry, to a stationary member of the gantry, arranged on the stationary side of the CT imaging system 100. By way of example, a selected subset of the generated detector data from the X-ray detector 114 may be pre-processed by the pre-processing circuitry 115 before storage on the data storage unit 116 and/or before main processing by the processing circuitry 118. In a particular example, the same subset of detector data or an at least partially different or completely different subset of detector data may be processed by the processing circuitry 118.

Figure 15:
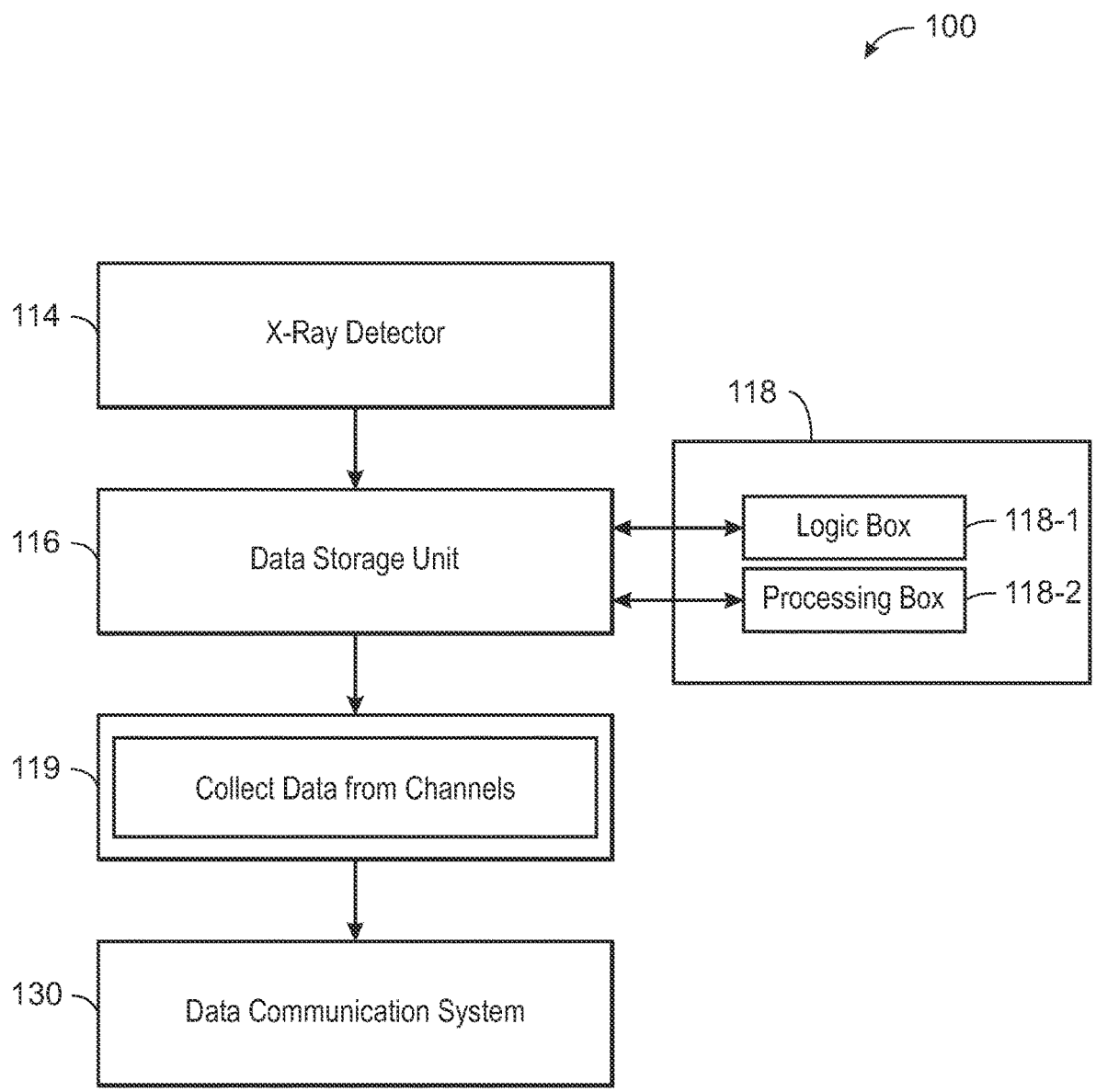
FIG. 15 is a schematic diagram illustrating an example of a method of operating a CT imaging system according to an embodiment.

FIG. 15 schematically shows another non-limiting example of a CT imaging system 100 according to an embodiment. In FIG. 15, the CT imaging system 100 comprises an X-ray detector 114, a data storage unit 116 and processing circuitry 118 arranged on the rotating side of the CT imaging system 100, e.g. on a rotating member of a gantry. Here, the generated detector data from the X-ray detector 114 is stored on the data storage unit 116 and/or processed by the processing circuitry 118 without being pre-processed. The processing circuitry 118 may comprise a logic box 118-1 and/or a processing box 118-2, wherein the processing box 118-2 may be configured to performer higher complexity computations compared to the logic box 118-1. The processing circuitry 118 may process at least part of the detector data on the data storage unit 116, and a data collector 119 may collect data, processed or non-processed, from all channels or a subset thereof and send it to the data communication system 130 which may then transfer the data from the rotating member of the gantry, to a stationary member of the gantry, arranged on the stationary side of the CT imaging system 100. This embodiment has certain technical advantages, as previously discussed. Effects and features of the second aspect are largely analogous to those described above in connection with the first aspect. Embodiments mentioned in relation to the first aspect are largely compatible with the second aspect. It is further noted that the inventive concepts relate to all possible combinations of features unless explicitly stated otherwise.

The invention claimed is:

1. A computed tomography (CT) imaging system comprising:
    a gantry including a rotating member on a rotating side and a stationary member on a stationary side;
    the rotating member on the rotating side comprising:
        an X-ray source configured to emit X-rays;
        an X-ray detector configured to generate detector data;
        a data storage unit configured to store the detector data;
        processing circuitry configured to process at least part of the stored detector data to generate a processed data set;
    the stationary member on the stationary side communicatively coupled to the rotating member on the rotating side;
    a data communication system configured to transfer the processed data set from the rotating member on the rotating side to the stationary member on the stationary side.

2. The CT imaging system according to claim 1, wherein the processed data set comprises a reduced data set.

3. The CT imaging system according to claim 1, wherein the processing circuitry is configured to operate in a plurality of output modes, each generating a respective processed data set.

4. The CT imaging system according to claim 3, wherein the plurality of output modes comprises an output mode for calibration and an output mode for patient imaging.

5. The CT imaging system according to claim 3, wherein the plurality of output modes generates respective processed data sets each being different from the others with respect to data size of the processed data set.

6. The CT imaging system according to claim 3, wherein an output mode is selected in response to a request to generate a corresponding processed data set using the selected output mode.

7. The CT imaging system according to claim 3, wherein the processing circuitry is configured to select a pre-determined output mode to generate a corresponding processed data set using the pre-determined output mode.

8. The CT imaging system according to claim 3, wherein the processing circuitry is configured to process the stored data using a set of consecutive output modes to generate respective processed data sets, and wherein the data communication system is configured to transfer the respective processed data sets consecutively.

9. The CT imaging system according to claim 1, wherein parts of a first processed data set is transferred via the data communication system, while other parts of the first processed data set is being generated, such that the processing of the detector data and the transferring of a processed data set from the rotating member on the rotating side to the stationary member on the stationary side is performed at least partially simultaneously.

10. The CT imaging system according to claim 1, wherein the data communication system comprises a first data communication unit on the rotating member on the rotating side and a second data communication unit on the stationary member on the stationary side.

11. The CT imaging system according to claim 1, wherein the data communication system comprises one or more slip rings.

12. The CT imaging system according to claim 1, wherein the X-ray detector is configured to send the detector data to the data storage unit, and wherein the data storage unit is configured to store an entirety of the generated detector data.

13. The CT imaging system according to claim 1, wherein the data storage unit is a non-volatile memory (NVMe) and/or a Random Access Memory (RAM).

14. The CT imaging system according to claim 1, wherein the data storage unit is a set of transitory registers that is a part of the data processing circuitry.

15. The CT imaging system according to claim 1, wherein the X-ray detector is a photon-counting detector.

16. The CT imaging system according to claim 1, wherein the X-ray detector is an energy-discriminating detector.

17. The CT imaging system according to claim 1, wherein the processing of the detector data, to generate a processed data set, comprises combining detector data.

18. The CT imaging system according to claim 1, wherein the processing circuitry is configured to process at least part of the generated detector data before the generated detector data is stored on the data storage unit.

19. The CT imaging system according to claim 1, wherein the system comprises, on the stationary member on the stationary side:

a second data storage unit, wherein the second data storage unit is configured to receive the processed data set from the rotating member on the rotating side, and a second set of processing circuitry, wherein the second set of processing circuitry is configured to process the received processed data set.

20. A method of operating a CT imaging system, the CT imaging system comprising:

a rotating side comprising:
    an X-ray source configured to emit X-rays;
    an X-ray detector;
    a data storage unit;
    processing circuitry; and a stationary side communicatively coupled to the rotating side via a data communication system;

wherein the method comprises:

generating detector data via the X-ray detector;

storing the detector data in the data storage unit;

processing the stored detector data, in the processing circuitry, to generate a processed data set;

transferring the processed data set from the rotating side to the stationary side via the data communication system.

21. The method according to claim 20, wherein the processed data set comprises a reduced data set.

* * * * *